US009301919B2

(12) United States Patent
Maskiewicz

(10) Patent No.: US 9,301,919 B2
(45) Date of Patent: Apr. 5, 2016

(54) SUBLIMABLE SUSTAINED RELEASE DELIVERY SYSTEM AND METHOD OF MAKING SAME

(75) Inventor: Richard Maskiewicz, Redlands, CA (US)

(73) Assignee: OAKWOOD LABORATORIES, LLC, Oakwood Village, OH (US)

(*) Notice: Subject to any disclaimer, the term of this patent is extended or adjusted under 35 U.S.C. 154(b) by 407 days.

(21) Appl. No.: 11/615,048

(22) Filed: Dec. 22, 2006

(65) Prior Publication Data

US 2007/0148098 A1 Jun. 28, 2007

Related U.S. Application Data

(60) Provisional application No. 60/753,114, filed on Dec. 22, 2005.

(51) Int. Cl.
*A61K 9/00* (2006.01)
*A61K 9/16* (2006.01)

(52) U.S. Cl.
CPC ............. *A61K 9/0024* (2013.01); *A61K 9/1617* (2013.01); *Y10S 514/957* (2013.01)

(58) Field of Classification Search
None
See application file for complete search history.

(56) References Cited

U.S. PATENT DOCUMENTS

| | | | |
|---|---|---|---|
| 3,608,549 A | 9/1971 | Merrill | |
| 3,903,022 A | 9/1975 | Ohara et al. | |
| 4,001,434 A | 1/1977 | Nakai et al. | |
| 4,045,551 A | 8/1977 | Ueno et al. | |
| 4,093,709 A | 6/1978 | Choi et al. | |
| 4,123,525 A | 10/1978 | Ueno et al. | |
| 4,138,344 A | 2/1979 | Choi et al. | |
| 4,210,640 A | 7/1980 | Ueno et al. | |
| 4,214,892 A | 7/1980 | Ueno et al. | |
| 4,233,161 A | 11/1980 | Sato et al. | |
| 4,301,043 A | 11/1981 | Sato et al. | |
| 4,389,330 A | 6/1983 | Tice et al. | |
| 4,400,532 A | 8/1983 | Lagow et al. | |
| 4,405,467 A | 9/1983 | Sato et al. | |
| 4,801,458 A | 1/1989 | Hidaka et al. | |
| 4,842,853 A * | 6/1989 | Gebauer et al. | 424/76.1 |
| 4,855,134 A | 8/1989 | Yamahira et al. | |
| 4,957,744 A | 9/1990 | della Valle et al. | |
| 5,023,082 A * | 6/1991 | Friedman et al. | 424/426 |
| 5,278,135 A | 1/1994 | Howard, Jr. et al. | |
| 5,352,662 A | 10/1994 | Brooks et al. | |
| 5,360,797 A * | 11/1994 | Johnson et al. | 514/111 |
| 5,411,951 A | 5/1995 | Mitchell | |
| 5,456,247 A | 10/1995 | Shilling et al. | |
| 5,518,731 A | 5/1996 | Meadows | |
| 5,578,709 A | 11/1996 | Woiszwillo | |
| 5,628,993 A | 5/1997 | Yamagata et al. | |
| 5,677,355 A | 10/1997 | Shalaby et al. | |
| 5,686,091 A | 11/1997 | Leong et al. | |
| 5,736,152 A | 4/1998 | Dunn | |
| 5,747,058 A | 5/1998 | Tipton | |
| 5,932,547 A | 8/1999 | Stevenson et al. | |
| 5,969,020 A | 10/1999 | Shalaby et al. | |
| 6,110,503 A | 8/2000 | Rickey et al. | |
| 6,143,276 A | 11/2000 | Unger | |
| 6,245,740 B1 | 6/2001 | Goldenberg et al. | |
| 6,261,601 B1 | 7/2001 | Talwar et al. | |
| 6,264,990 B1 | 7/2001 | Knepp et al. | |
| 6,395,300 B1 | 5/2002 | Straub et al. | |
| 6,527,762 B1 | 3/2003 | Santini, Jr. et al. | |
| 2002/0001617 A1 * | 1/2002 | Lee et al. | 424/465 |
| 2004/0034357 A1 | 2/2004 | Beane et al. | |
| 2004/0137070 A1 * | 7/2004 | Scherzer et al. | 424/489 |
| 2005/0043816 A1 | 2/2005 | Datta et al. | |
| 2005/0143416 A1 | 6/2005 | Kruk et al. | |
| 2006/0099245 A1 | 5/2006 | Kumar et al. | |
| 2007/0148098 A1 | 6/2007 | Maskiewicz | |

FOREIGN PATENT DOCUMENTS

| | | |
|---|---|---|
| CN | 1075844 | 9/1993 |
| CN | 1102299 | 5/1995 |
| JP | 54-046847 | 4/1979 |
| JP | 61-066777 | 4/1986 |
| JP | 02-280771 | 11/1990 |
| JP | 2003125706 A * | 5/2003 |
| JP | 2004202370 A * | 7/2004 |
| WO | 0110419 | 2/2001 |
| WO | WO2007109530 | 9/2007 |

OTHER PUBLICATIONS http://hyperphysics.phy-astr.gsu.edu/Hbase/organic/alkane.html, Alkanes, printed Jun. 12, 2008, http://hyperphysics.phy-astr.gsu.edu/Hbase/organic/alkane.html, 1 page.*
www.yourdictionary.com—drawn from the American Heritage Medical Dictionary, granule, 2009 printed Jan. 15, 2010 from http://www.yourdictionary.com/medical/granule, 2 pages.*
Merriam-Webster Online Dictionary, pellet, printed from http://www.merriam-webster.com/dictionary/pellet on Jan. 16, 2010, 2 pages.*
Chickos et all, Enthalpies of Sublimation of Organic and Organometallic Compounds. 1910-2001, J. Phys. Chem. Ref. Data 31, 537-698 (2002).*
L-(−)-Menthol, ChemSpider, 2015, printed from http://www.chemspider.com/Chemical-Structure.15803.html, 3 pages.*
Silva et al, Analgesic and anti-inflammatory effects of essential oils of Eucalyptus, J Ethnopharmacol. Dec. 2003;89(2-3):277-83, printed from http://www.ncbi.nlm.nih.gov/pubmed/14611892, abstract only, 1 page.*

(Continued)

*Primary Examiner* — Gigi Huang
(74) *Attorney, Agent, or Firm* — Pearne & Gordon LLP

(57) ABSTRACT

The invention relates to compositions suitable for the delivery and/or stabilization of biologically active substances. The compositions comprise a sublimable matrix material and the biologically active agent to be delivered. The compositions can be used as drug delivery systems to treat a wide variety of diseases or as systems for the protection and stabilization of such substances. Also disclosed are methods for preparing compositions of the present invention.

10 Claims, 13 Drawing Sheets

(56) References Cited

OTHER PUBLICATIONS

German L. Perlovich et al., "Thermodynamics of sublimation, crystal lattice energies, and crystal structures of racemates and enantiomers: (+)- and (±)-iburpofen," J. Pharm. Sci, vol. 93, No. 3, 2004, abstract.

Kelly L. Smith et al., "Bioerodible polymers for delivery of macromolecules," Advanced Drug Delivery Reviews, 4 (1990)343-357.

Cynthia L. Stevenson, "Characterization of protein and peptide stability and solubility in non-aqueous solvents," Current Pharmaceutical Biotechnology, 2000, 1, 165-182.

Minli Xie et al., "Sublimation characterization and vapor pressure estimation of an HIV nonnucleoside reverse transcriptase inhibitor using thermogravimetric analysis," AAPS PharmSciTech 2003; 4 (2) Article 23 (http://www.pharmscitech.org).

P. Caravatti et al., "Direct evidence of microscopic homogeneity in disordered solids," J. Am. Chem. Soc. 1982, 104, 5506-5507.

R. van Dijkhuizen-Radersma et al., "In vitro/in vivo correlation for 14C-methylated lysozyme release from poly (ether-ester) microspheres," Pharmaceutical Research, vol. 21, No. 3, Mar. 2004.

F. Lecomte et al., "rh-Interferon α-2a release from Triglyceride-based Matrices: experiment and theory," © 2005 Controlled Release Society 32nd Allual Meeting & ExpositioN Transactions, #410.

German L. Perlovich et al., "Solvation and hydration characteristics of ibuprofen and acetylsalicylic acid," AAPA PharmSci 2004; 6 (1) Article 3 (http://www.aapspharmsci.org).

International Search Report and Written Opinion of the International Searching Authority (PCT/US2006/062529) dated Sep. 12, 2007.

http://hyperphysics.phy-astr.gsu.ed/Hbase/organic/alkane.html, Alkanes, printed Jun. 12, 2008, http://hyperphysics.phy-astr.gsu.edu/Hbase/organic/alkane.html, 3 pages.

\* cited by examiner

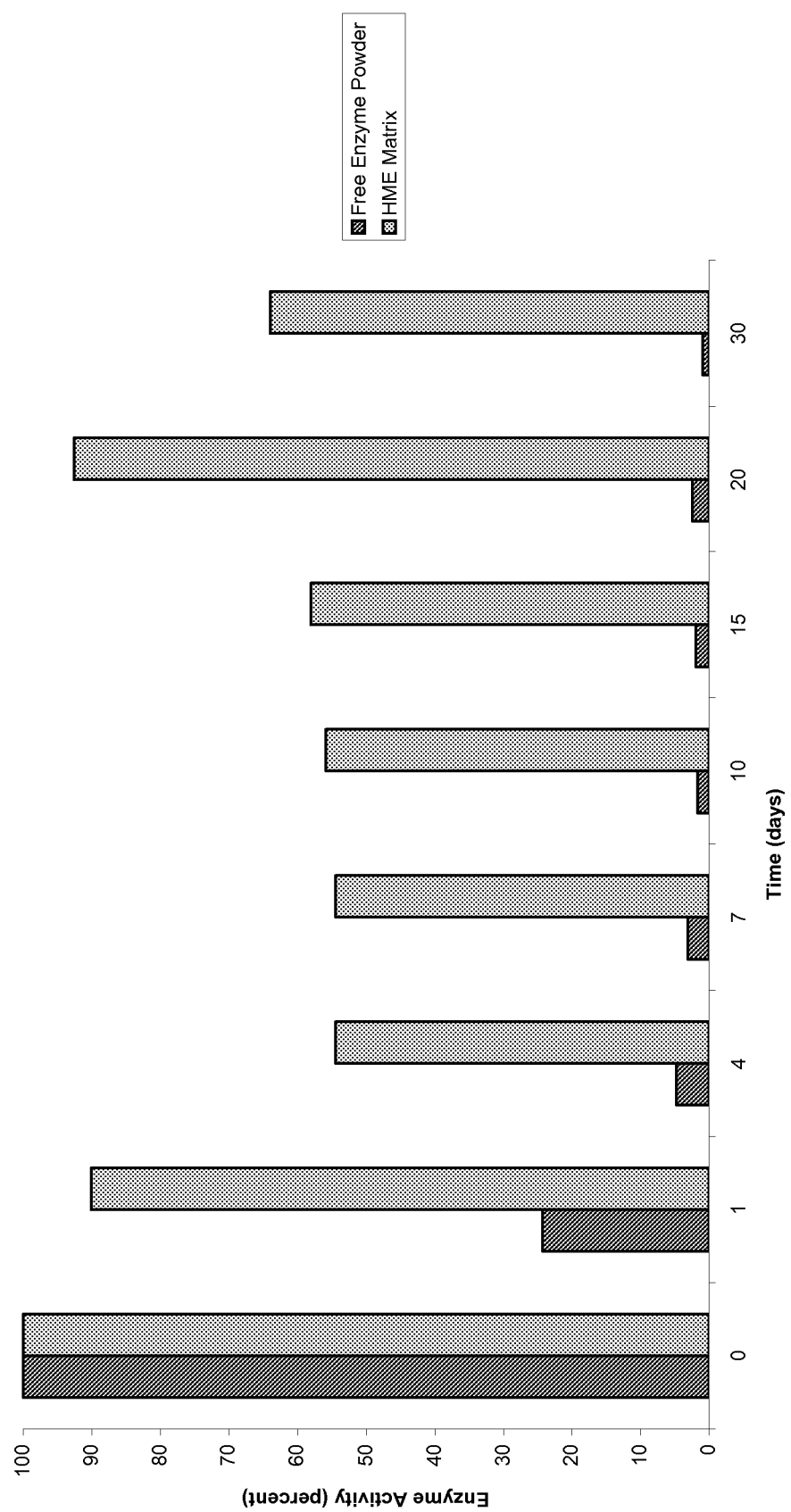

SUBLIMABLE SUSTAINED RELEASE DELIVERY SYSTEM AND METHOD OF MAKING SAME

CROSS-REFERENCE TO RELATED APPLICATION

This application claims the benefit of U.S. Provisional Patent Application No. 60/753,114 filed Dec. 22, 2006, which is incorporated herein by reference in its entirety.

BACKGROUND OF THE INVENTION

In the past few decades, there has been extensive research in the area of bioerodable matrices for the controlled release of bioactive compounds. These systems are of interest not only because they provide for the sustained release of therapeutic compounds, thereby increasing patient compliance, but also because they obviate the need to retrieve the carrier system after drug depletion.

The most common materials utilized for these matrices are biodegradable polymers, which are manufactured either as implantable devices or as suspensions of drug-containing polymeric microparticles. Synthetic polymers contemplated for use as matrices include those comprised of polylactic acid or copolymers of lactic and glycolic acids, polyanhydrides, polyamides, polyorthoesters, and polyphosphazenes (see e.g., U.S. Pat. Nos. 4,389,330, 4,093,709, 4,138,344; and Smith et al., *Adv. Drug Del. Rev,* 1990). Biodegradable polymers of biological origin are also well known, for example Yamahira in U.S. Pat. No. 4,855,134 discloses the sustained-release of α-interferon from matrices of gelatin, collagen and albumin. Woiszwillo in U.S. Pat. No. 5,578,709 teaches the use of matrices comprised of dehydrated, crosslinked proteins or polysaccharides for the release of many types of drugs, including macromolecules. Hyaluronic acid has also been crosslinked and used as a degradable swelling polymer for drug delivery applications (U.S. Pat. No. 4,957,744 to Della Valle et al).

Non-polymeric in-situ forming implant systems have also been disclosed (U.S. Pat. No. 5,736,152 to Dunn and U.S. Pat. No. 5,747,058 to Tipton and Holl). In these systems, a non-polymeric, biodegradable carrier material is dissolved in an organic solvent into which drug has been either dispersed or dissolved to form a liquid. Upon injection into the body the organic solvent dissipates, thereby producing a solid implant from which drug is released. Exemplary non-polymeric carriers disclosed are cholesterol and its derivatives, various fatty acids and fatty acid alcohols, phospholipids and derivatives thereof, sucrose acetate isobutyrate, and long-chain fatty acid amides. Other non-polymeric implants utilizing triglyceride-based matrices, oligoglycerol esters of fatty acids, and various vegetable (sesame, soy, peanut oils etc.) or synthetic (miglyol) oils gelled with aluminum mono-fatty acid esters (U.S. Pat. Nos. 5,411,951, 5,628,993 and 5,352,662) have also been described.

Proteins, peptides, polypeptides and other proteinaceous substances (e.g., viruses, antibodies), collectively referred to herein as proteins, have great utility as therapeutic agents in the prevention, treatment, and diagnosis of diseases. Unfortunately, these molecules possess limited stability, and are susceptible to both chemical degradation (e.g., via deamidation, oxidation, hydrolysis, disulfide exchange, and racemization of chiral amino acid residues) and physical degradation (e.g., via denaturation, aggregation, and precipitation), often resulting in a loss of biological activity. It is no surprise, therefore, that the delivery of these molecules from prior art systems has met with limited success. For example, the delivery of proteins from polyester-based implants and microspheres often leads to their chemical inactivation due to the acidic environment that develops during matrix erosion, and/or to their physical degradation due to adsorption to the polyester matrix surface. In other cases, either the presence of water or the partial hydrophilicity of the matrix makes it difficult to guarantee that water mediated degradation and/or denaturation processes would not occur either in-situ or in environments, such as the subcutaneous space, where contact with and imbibement of water is possible. And, although oleaginous delivery vehicles might theoretically protect protein drugs from aqueous degradation pathways (hydrolysis, deamidation, racemization etc.), many of the vehicles themselves are, to limited degrees, hydrophilic and unstable at body temperature. For example, the storage of liquid vegetable oils at physiological temperatures can result in the formation of amphiphilic and reactive species such as free fatty acids and peroxides (a process accelerated by the presence of traces of various metal ions such as copper or iron) which, in turn will catalyze the oxidative degradation or structural degradation of many proteins.

In addition, certain drugs, for example cytotoxic agents, cannot currently be developed as controlled release oral pharmaceutical products due to their high reactivity (low stability) in excipients typically employed for achieving sustained release from tablets or capsules. The alternative, parenteral delivery (often after reconstitution of lyophilized material), or an immediate-release oral formulation, may present efficacy or toxicity issues due to rapid fluctuations in plasma levels. Convenience and compliance issues can arise if multiple injections or tablets/capsules are required daily.

Consequently, there is a need to develop compositions, devices or systems that can overcome these limitations of the prior art. Such compositions should maintain the stability of the active compound at both room temperature and at body temperature (i.e., at 25 and 37° C.) for prolonged periods, and provide for the sustained release of active agents, such as reactive or unstable bioactive therapeutic agents.

SUMMARY OF THE INVENTION

A novel, chemically inert drug delivery system has been discovered which provides for the sustained release of biologically active agents in-vivo by the sublimation of the surrounding matrix material, rather than by dissolution, hydrolysis or chemically driven matrix erosion. The matrix material is usually substantially water insoluble and chemically inert, having little or no oxidative or hydrolytic reactivity. Thus, although there will possibly be at least some initial diffusional drug release, and subsequent partial drug release by matrix erosion resulting from conventional dissolution or chemical degradation mechanisms, the release of a significant amount, and usually substantially all of the therapeutic agent is achieved from the composition of the present invention without being dependent on these well-known mechanisms. Rather, the rate and duration of release of a therapeutic agent from a composition of the present invention relies on the enthalpy of sublimation ($\Delta H_{sub}$) of the substances used for matrix preparation. The enthalpy of sublimation of the matrix material results in a specific vapor pressure at body temperature. Matrix erosion by sublimation with concomitant exposure of drug dispersed in the matrix would then be a function of achieved vapor pressure and environmental (for example, injection/implantation site) convection.

One advantage of the current invention is that the sublimable matrix material provides for a hydrophobic environment of low intrinsic and water-mediated reactivity, thus protecting the therapeutic agent from both chemical and physical degradation. This allows for the sustained release of active agents, and especially unstable or reactive biological agents in plants and animals, including humans, that would not otherwise be feasible. It has also been advantageously discovered that by judicious selection of sublimable matrix materials a wide variety of sublimation rates and, as a consequence, release rates of the biologically active agent can be achieved. Accordingly, in one embodiment, the composition comprises a sublimable matrix material and a biologically active agent.

It has also been advantageously discovered that the release rate of a biologically active agent can be modulated by the blending of sublimable matrix materials possessing different enthalpies of sublimation. Consequently, in an alternative embodiment, the composition comprises a mixture of sublimable matrix materials and a biologically active agent.

In yet another embodiment, the composition will further comprise an excipient, which will modify the release of the biologically active agent from the sublimable matrix—a "sublimation rate modifier". The sublimation rate modifier may act to modify the release rate of the biologically active agent e.g., either by affecting the net vapor pressure of the sublimable matrix material, or by altering the surface area, such as by forming pores within the sublimable matrix material. This allows manipulation not only of the rate of release of the biologically active agent from the matrix, but also of the release profile. For example, by using a pore-forming sublimation rate modifier a release profile may be obtained in which a burst of biologically active agent is released, which is followed by a substantially linear release profile. Consequently, in yet another embodiment the composition comprises a sublimable matrix material, or mixtures thereof, a sublimation rate modifier, and a biologically active agent.

Thus, another advantage of the present invention is that both the rate of release and the release profile of biologically active agents from the matrix is easily manipulated either by blending sublimable matrix materials with differing sublimation rates, or by adding sublimation rate modifiers. Of course, in some embodiments, the composition of the invention can be combined or employed with other materials, such as coatings, that will affect release by other conventional mechanisms.

In yet still another aspect, the invention provides methods for preparing compositions comprising a sublimable matrix material or mixtures thereof, a biologically active agent, and optionally a sublimation rate modifier. In one embodiment, a sublimable matrix material and a biologically active agent are intimately mixed, then compressed into an implant of the desired shape, such as a rod, cylinder or disc.

In yet another aspect, the invention provides for a method of delivering to an animal a biologically active agent, said method comprising administering to said animal an effective amount of a composition comprising a sublimable matrix material and a biologically active agent.

DESCRIPTION OF THE DRAWINGS

FIG. 1 shows graphically the sublimation rates of various sublimable matrices, determined gravimetrically under defined convective conditions at room temperature. Sublimation rates, expressed as the percent of pellet mass remaining versus time, are shown for perfluoroneopentane (PFNP), norbornane (NOR), hexamethylethane (HME), hexamethylcyclotrisiloxane (HCMS), perfluoroadamantane (PFA) and adamantane (ADM) matrices.

FIG. 2 shows graphically the sublimation rates, determined gravimetrically under freely convective conditions, of pure sublimable matrices, and various mixtures thereof. Sublimation rates, expressed as the percent of pellet mass remaining versus time, are shown for matrices comprised of pure HME, PFA and ADM, as well as for matrices comprising various mixtures of HME, PFA and ADM.

FIG. 3 shows graphically the effect of the release rate modifier perfluorodecalin (PFD) on the sublimation rate of PFNP matrices.

FIG. 4 shows graphically the equivalence of the sublimation rate of HME pellet-type matrices (plotted as the percent of HME matrix weight loss versus time), to the release rate of BPB from HME pellet-type matrices into distilled water partially open to the atmosphere (plotted as the percent of BPB release versus time).

FIG. 5 shows graphically the equivalence of readily dissolvable bromophenol blue (BPB) from HME disc-type matrices (plotted as the percent of BPB release versus time) to the sublimation rate of HME disc-type matrices into air under good convection conditions (plotted as the percent of HME matrix weight loss versus time).

FIG. 6 shows graphically the equivalence of the release rate of readily dissolvable BPB into distilled water from ADM disc-type matrices (plotted as the percent of BPB release versus time) to the sublimation rate of ADM disc-type matrices into air under good convection conditions (plotted as the percent of HME matrix weight loss versus time).

FIG. 7 shows graphically the equivalence of the sublimation rate of HME pellet-type matrices ("HME weight loss"), to the release rates of betamethasone (BMS) from HME pellet-type matrices into distilled water partially open to the atmosphere ("BMS sublimation release"). In contrast, the figure graphically illustrates the large difference in the release rate of BMS under conditions where sublimation can occur ("BMS sublimation release") versus that which occurs under conditions where sublimation of the pellet cannot occur, i.e. water filled closed containers, thus limiting the release of BMS from HME pellets to that which can diffuse through the pellet matrix ("BMS diffusion-constrained release").

FIG. 8 shows graphically the equivalence of the sublimation rate of ADM pellet-type matrices ("ADM weight loss"), to the release rates of BMS from ADM pellet-type matrices into distilled water partially open to the atmosphere ("BMS sublimation release"). In contrast, the figure graphically illustrates the large difference in the release rate of BMS under conditions where sublimation can occur ("BMS sublimation release") versus that which occurs under conditions where sublimation of the pellet cannot occur, i.e. water filled closed containers, thus limiting the release of BMS from ADM pellets to that which can diffuse through the pellet matrix ("BMS diffusion-constrained release").

FIG. 9 shows graphically the equivalence of the sublimation rate of 50/50 HME/ADM pellet-type matrices ("50/50 Mixture weight loss"), to the release rates of BMS from 50/50 HME/ADM pellet-type matrices into distilled water partially open to the atmosphere ("BMS sublimation release"). In contrast, the figure graphically illustrates the large difference in the release rate of BMS under conditions where sublimation can occur ("BMS sublimation release") versus that which occurs under conditions where sublimation of the pellet cannot occur, i.e. water filled closed containers, thus limiting the release of BMS from 50/50 HME/ADM pellets to that which can diffuse through the pellet matrix ("BMS diffusion-constrained release").

FIG. 10 shows graphically the modulation of BMS release by the blending of different sublimable matrix materials.

FIG. 13 shows graphically the comparison of enzyme activity lost by alkaline phosphatase when stored: (a) as the formulated lyophilized powder at 37° C. and 100% humidity, or (b) as the lyophilized powder incorporated into HME matrices and stored in aqueous solution at 37° C.

DETAILED DESCRIPTION OF THE INVENTION

Figure 1:
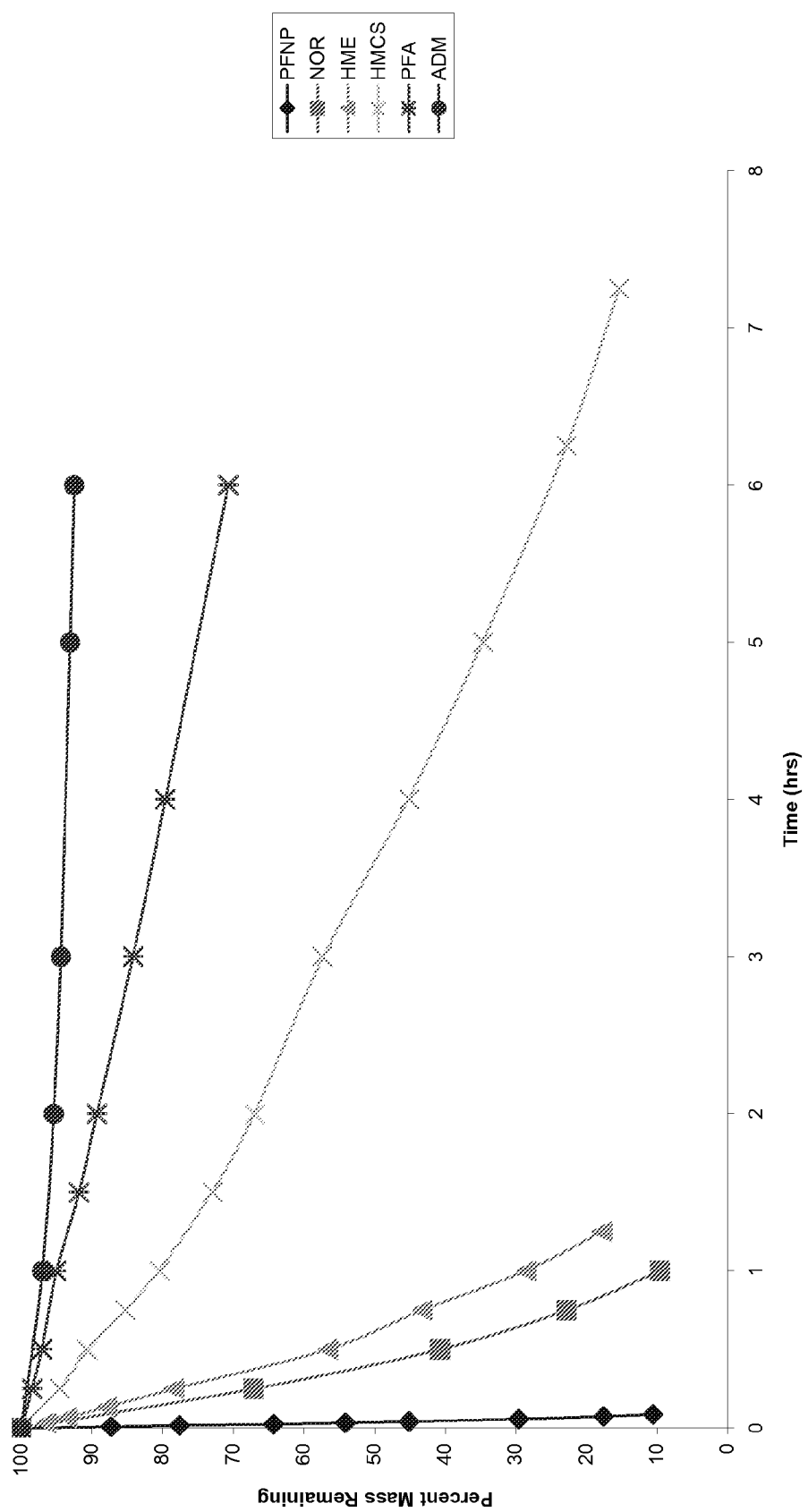

As used herein, the term "sublimable matrix material" refers to any compound that transforms from a solid or semi-solid to a gas in the environment of use, such as the human body. It will usually be essentially water-insoluble and more volatile than the active agent. Sublimable matrix materials useful in the invention include materials that are solid or semi-solid at body temperature and have an enthalpy of sublimation ($\Delta H_{sub}$) of about 20 kJ/mole to about 100 kJ/mole. In certain embodiments, such materials will have a melting point above about 37° C. Preferred sublimable matrix materials typically comprise multi-branched or multicyclic alkanes or perfluoroalkanes, which are essentially spherical, globular, or oval in shape and possess enthalpies of sublimation which allow desirable and controlled rates of matrix erosion. The sublimable matrix material is preferably biocompatible, e.g., it should not be toxic or otherwise cause adverse tissue reactions.

Examples of sublimable matrix materials include, but are not limited to, globular alkanes (i.e., alkane molecules possessing a spherical, ellipsoid or ball-like shape), perfluorinated alkanes, globular perfluorinated alkanes, adamantane, perfluoroadamantane, 1-methyladamantane, perfluoro 1-methyladamantane, tetraisopropylmethane, perfluorotetraisopropylmethane, 2,2,3,3-tetramethylbutane (hexamethylethane), perfluoro-2,2,3,3-tetramethylbutane, perfluoroneopentane, perfluoro-C60 fullerene, cubane, perfluorocubane, octamethylcubane, perfluorooctamethylcubane, perfluoromethyladamantanes, perfluorotri-tert-butylmethane, perfluorodimethyladamantane, perfluorohexamethylethane, perfluoro-1,3-dimethyladamantane, isocamphane, tricyclene, 1-ethyladamantane, 1-methyldimantane, perfluorodimethylbicyclo[3.3.1]nonane, diadamantane, perfluorodiadamantane, tri-tert-butylmethane, norbornane, perfluoronorbornane, cyclododecane, perfluorocyclododecane, hexamethylcyclotrisiloxane, perfluoroundecane, perfluorododecane, bicycle[3.3.1]nonane, tetracycloheptane, tricyclohexane, dimethyl-isopropyl-perhydrophenanthrene, hexamethylprismane, prismane, tetracyclododecane, bicyclo[3.3.3]undecane, 2-methyladamantane, 1-methyladamantane, pentacycloundecane, tricyclodecane, bicyclodecane, bicyclo[3.3.1]nonane, bicyclo[2.2.2]octane, bicyclo[2.2.1]heptane, perfluorotri-tert-butylmethane, perfluoro-1,3,5-trimethyladamantane, perfluoro2,2-dimethyladamantane, perfluorotetracycloheptane, perfluorotricyclohexane, perfluorohexamethylprismane, perfluoroprismane, perfluorotetracyclododecane, perfluorobicyclo[3.3.3]undecane, perfluoro2-methyladamantane, perfluoropentacycloundecane, perfluorotricyclodecane, perfluorobicyclodecane, perfluorobicyclo[3.3.1]nonane, perfluorobicyclo[2.2.2]octane, perfluorobicyclo[2.2.1]heptane, and any mixtures of the foregoing. Other suitable materials will be apparent to those of ordinary skill in the art in view of the instant disclosure.

In one particular aspect of the invention, adamantane is used as the sublimable matrix material. Adamantane is a globular alkane with a melting point of 270° C. and a sublimation enthalpy of 59 kJ/mole. Other embodiments use matrices comprised of hexamethylethane (melting point 100° C., $\Delta H_{sub}$ 43 kJ/mole), perfluoroneopentane (melting point 72° C., $\Delta H_{sub}$ <25 kJ/mole), norbornane (melting point 88° C., $\Delta H_{sub}$ 40 kJ/mole), hexamethylcyclotrisiloxane (melting point 60° C., $\Delta H_{sub}$ 54 kJ/mole), cyclododecane ((melting point 61° C., $\Delta H_{sub}$ 76 kJ/mole) or mixtures thereof.

As defined herein, the term "sublimation rate modifier" refers to a molecule or molecules added to the sublimable matrix material in order to alter the rate of release of a therapeutic agent, such as by altering the rate of sublimation or by altering the physical structure of the matrix. A sublimation rate modifier may or may not be sublimable, and may be a solid or a liquid at physiological temperatures. The addition of sublimation rate modifiers to the matrix provides a range of in-vivo release characteristics of the biologically active agent. The sublimation rate modifier may be homogenously dispersed throughout the composition to affect the rate of sublimation by altering the net vapor pressure of the matrix, or it may be heterogeneously dispersed in the matrix to induce the formation of pores, which would increase the surface area of the matrix and its concomitant erosion rate, thereby facilitating drug release.

The sublimation rate modifier is present in the composition in any amount that achieves the desired affect. Typically, the sublimation rate modifier is present in the composition in the range from about 0.1 percent to about 30 percent by weight relative to the total weight of the composition, and more typically, between approximately 0.5 percent to about 10 percent by weight. Higher amounts may be present when the sublimation rate modifier is itself sublimable.

Examples of suitable sublimation rate modifiers include, but are not limited to, trimethylacetamide, 2,2-dimethyl-1,3-propanediol, neopentylpivalate, perfluorodecalin, perfluoroalkanes, tri-tert-butylmethanol, perfluorocycloalkanes, camphor, camphene, neo-pentyl alcohol, hexachloroethane, chlorobutanol, menthol, terpin hydrate, vanillin, ethyl vanillin, 1,3,5-trioxane, naphthalene, phenol, tristearin, dextran, glycogen, tert-butanol, biodegradable polymers such as, but not limited to, those comprised of polylactic acid or copolymers of lactic and glycolic acids, polyorthoesters, or polyanhydrides, microparticles comprised of bioerodable polymers (such as, for example comprised of polylactic acid or copolymers of lactic and glycolic acids, polyorthoesters, polyanhydrides), fatty acids, polyvinylpyrrolidone, polyethyleneglycol, polyvinyl alcohol, polyacrylic acid, cholesterol and microparticles thereof, caprostane, triglycerides having a melting point above 37° C., collagen and microparticles thereof, gelatin and microparticles thereof, ethanol, propylene glycol, PEG 400, glycerol, polyglycerol, polysorbates, sucralose, and/or sucralose pentahydrate, and mixtures of any of the foregoing. Other suitable materials will be apparent to those of ordinary skill in the art in view of the instant disclosure.

As used herein, the term "matrix" denotes a solid phase carrier within which the active agent can be dispersed. The matrix can be any desired shape, such as sphere, spheroid, discoid, cylinder, rod, sheet and the like, or consistency, such as solid, malleable, deformable, flowable, and the like. The matrix may comprise a sublimable matrix material or a blend of sublimable matrix materials, and may optionally include a sublimation rate modifier.

Any substance that exhibits a desired property can be delivered using the composition of the present invention; preferably, the substance is one that is biologically active. The terms "biologically active substance", "drug", and "therapeutic agent" are used interchangeably herein and refer to any natural or synthetic, organic or inorganic molecule or mixture thereof, including a drug, peptide, polypeptide, protein, carbohydrate (including monosaccharides, oligosaccharides, and polysaccharides), nucleoprotein, mucoprotein, lipoprotein, or a small molecule complexed or linked to a protein, glycoprotein, steroid, nucleic acid (any form of DNA, including cDNA, or RNA, or a fragment thereof), nucleotide, nucleoside, oligonucleotides, gene construct, lipid, hormone, vitamin, cytotoxic agent, nutrient or combination thereof, that causes a biological effect when administered in vivo to a plant or animal, including but not limited to birds and mammals, including humans. These terms also refer to any substance used internally or externally as a medicine for the treatment, cure, or prevention of a disease or disorder, and includes but is not limited to antihypertensive agents, anti-infective agents (including antibiotics, antivirals, and antifungals), anthelmintics, anticonvulsants, antidiabetic agents, antimalarials, antimuscarinic agents, antineoplastic agents, immunomodulators, antioxidants, anesthetics, analgesics, protease inhibitors, chemotherapeutic agents, steroids, hormones, cardiac agents (including inotropic agents, alpha and beta adrenergic agonists and antagonists, narcotic antagonists, chelating agents, decongestants, radiopharmaceutical agents, vaccines and antisera, antiproliferatives, antihistamines, anticoagulants, antiphotoaging agents, melanotropic peptides, nonsteroidal and steroidal anti-inflammatory compounds, antipsychotics, anxiolytics, vitamins, parasympathoimetric agents, growth factors, enzymes, prodrugs, prohormones, appetite supressants/stimulants and combinations thereof, contraceptive agents, anti-Parkinson antispasmodics, vasodilators, thrombolytic agents thyroid agents, sympathomimetics, skeletal muscle relaxants, anti-asthma agents, antiangina agents, hypothalamic and pituitary hormones, gastrointestinal agents, diuretics, calcium regulating agents, antithyroid agents, antiprotozoal agents, antimigraine agents, antigout agents, dermatological agents, corticosteroids, diagnostic agents, and radiation absorbers, including UV-absorbers.

Examples of drugs, biologically active agents or therapeutic agents include, but are not limited to: risperidone, olanzapine, clozapine, quetiapine, and ziprasidone, nitrofurazone, sodium propionate, penicillin, tetracycline, oxytetracycline, chlorotetracycline, bacitracin, nystatin, streptomycin, neomycin, polymyxin, gramicidin, chloramphenicol, erythromycin, and azithromycin; sulfonamides, idoxuridine; antazoline, methapyritene, chlorpheniramine, pyrilamine prophenpyridamine, hydrocortisone, cortisone, hydrocortisone acetate, betamethasone, dexamethasone, dexamethasone 21-phosphate, fluocinolone, triamcinolone, medrysone, prednisolone, prednisolone 21-sodium succinate, and prednisolone acetate; desensitizing agents such as ragweed pollen antigens, hay fever pollen antigens, dust antigen and milk antigen; vaccines such as smallpox, yellow fever, distemper, hog cholera, chicken pox, antivenom, scarlet fever, diphtheria toxoid, tetanus toxoid, pigeon pox, whooping cough, influenza rabies, mumps, measles, poliomyelitis, and Newcastle disease; decongestants such as phenylephrine, naphazoline, and tetrahydrazoline; miotics and anticholinesterases such as pilocarpine, esperine salicylate, carbachol, diisopropyl fluorophosphate, phospholine iodide, and demecarium bromide; parasympatholytics such as atropine sulfate, cyclopentolate, homatropine, scopolamine, tropicamide, eucatropine, and hydroxyamphetamine; sympathomimetics such as epinephrine; pentobarbital sodium, phenobarbital, secobarbital sodium, codeine, (α-bromoisovaleryl)urea, carbromal; psychic energizers such as 3-(2-aminopropyl)indole acetate and 3-(2-aminobutyl)indole acetate; reserpine, chlorpromayline, thiopropazate; methyl-testosterone and fluorymesterone; estrogens such as estrone, 17-beta.-estradiol, ethinyl estradiol, and diethylstilbestrol; progestational agents such as progesterone, megestrol, melengestrol, chlormadinone, ethisterone, norethynodrel, 19-norprogesterone, norethindrone, medroxyprogesterone and 17-.beta.-hydroxy-progesterone; analgesics such as fentanyl, sufentanyl, meperidine; local anasthetics such as bupivicaine, lidocaine; antipyretics such as aspirin, sodium salicylate, and salicylamide; antispasmodics such as atropine, methantheline, papaverine, and methscopolamine bromide; antimalarials such as the 4-aminoquinolines, 8-aminoquinolines, chloroquine, and pyrimethamine, antihistamines such as diphenhydramine, dimenhydrinate, tripelennamine, perphenazine, and chlorphenazine; cardioactive agents such as dibenzhydroflume thiazide, flumethiazide, chlorothiazide, and aminotrate; nutritional agents such as vitamins.

Examples of protein, peptide, and proteinaceous drugs which may be formulated using the present invention include those proteins/peptides/proteinaceous compounds which have biological activity or which may be used to treat a disease or other pathological condition. They include, but are not limited to growth hormone, Factor VIII, Factor IX and other coagulation factors, chymotrypsin, trypsinogen, interferon, beta-galactosidase, lactate dehydrogenase, growth factors, clotting factors, enzymes, immune response stimulators, cytokines, lymphokines, interferons, immunoglobulins, interleukins, peptides, somatostatin, somatotropin analogues, somatomedin-C, gonadotropic releasing hormone, follicle stimulating hormone, luteinizing hormone, LHRH, LHRH analogues such as leuprolide, nafarelin and goserelin, LHRH agonists and antagonists, growth hormone releasing factor, calcitonin, colchicine, gonadotropins such as chorionic gonadotropin, oxytocin, octreotide, somatotropin plus an amino acid, vasopressin, adrenocorticotrophic hormone, epidermal growth factor, prolactin, somatotropin plus a protein, cosyntropin, lypressin, polypeptides such as thyrotropin releasing hormone, thyroid stimulation hormone, secretin, pancreozymin, enkephalin, glucagon, endocrine agents secreted internally and distributed by way of the bloodstream, and the like. Further agents that may be delivered include a, antitrypsin, insulin and other peptide hormones, adrenal cortical stimulating hormone, thyroid stimulating hormone, and other pituitary hormones, interferon-alpha., -beta., and -gamma., consensus interferon, erythropoietin, growth factors such as GCSF, GM-CSF, insulin-like growth factor 1, tissue plasminogen activator, CF4, dDAVP, tumor necrosis factor receptor, pancreatic enzymes, lactase, interleukin-1 receptor antagonist, interleukin-2, tumor suppresser proteins, cytotoxic proteins, retroviruses and other viruses, viral proteins, antibodies, recombinant antibodies, antibody fragments and the like.

The protein, peptide and nucleic acid compounds useful in the formulations and methods of the present invention can be used in the form of a salt, preferably a pharmaceutically acceptable salt. Alternatively, these agents can be PEGylated or conjugated with adducts such as carbohydrates.

Examples of nucleic acid compounds that may be formulated using the present invention include those nucleic acids that code for proteins which have biological activity or which may be used to treat a disease or other pathological condition, such as the protein compounds listed above. Nucleic acids, including sense or antisense oligonucleotides, which block or reduce production of unwanted proteins are also useful in the present invention. Also included in nucleic acids which may be used in the present invention are those which, either directly or by coding for a protein, stimulate an animal to produce immunity against a disease condition (e.g., cancer) or infection by a pathogenic organism such as a bacteria, virus or protozoa.

The above agents are useful for the treatment or prevention of a variety of conditions including but not limited to hemophilia and other blood disorders, growth disorders, diabetes, leukemia, hepatitis, renal failure, HIV infection, hereditary diseases such as cerebrosidase deficiency and adenosine deaminase deficiency, hypertension, septic shock, autoimmune diseases such as multiple sclerosis, Graves disease, systemic lupus erythematosus and rheumatoid arthritis, shock and wasting disorders, cystic fibrosis, lactose intolerance, Crohn's disease, inflammatory bowel disease, gastrointestinal and other cancers. Analogs, derivatives, antagonists, agonists and pharmaceutically acceptable salts of the above may also be used.

In one embodiment the therapeutic agent to be delivered is an antigen, such that the composition acts a vaccine. The antigen can be derived from a cell, bacteria, or virus particle, or portion thereof. As defined herein, antigen may be a protein, peptide, polysaccharide, glycoprotein, glycolipid, nucleic acid, or combination thereof, which elicits an immunogenic response in an animal, for example, a mammal, bird, or fish. Examples of preferred antigens include viral proteins such as influenza proteins, human immunodeficiency virus (HIV) proteins, and hepatitis A, B, or C proteins, and bacterial proteins, lipopolysaccharides such as gram negative bacterial cell walls and *Neisseria gonorrhea* proteins, and parvovirus. The immunogenic response elicited can be humoral or cell-mediated. In the event the material to which the immunogenic response is to be directed is poorly antigenic, it may be conjugated to a carrier or to a hapten, using standard covalent binding techniques, for example, with one of the several commercially available reagent kits.

The therapeutic agent is included in the composition in an amount sufficient to deliver to the host animal or plant an amount to achieve a desired effect. The amount of drug or biologically active agent incorporated into the composition depends upon the desired release profile, the concentration of drug required for a biological effect, and the desired time period for release of the drug. Additionally, the amount of the therapeutic agent in the composition will also depend on the pharmacokinetics and pharmacodynamics of the therapeutic agent, as well as other factors known to those of skill in the art. It is to be noted that dosage values will also vary with the severity of the condition to be alleviated. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed invention. The composition may be administered in one dosage, or may be divided into a number of smaller doses to be administered at varying intervals of time.

The biologically active agent is typically present in the composition in the range from about 0.05 percent to about 90 percent by weight relative to the total weight of the composition. In some embodiments the biologically active agent is present in the range from about 0.1 percent to about 40 percent by weight relative to the total weight of the composition, and in still further embodiments, between approximately 0.5 percent to about 20 percent by weight. Larger amounts e.g., in excess of 90%, of the biologically active agent may be present by weight when the composition is employed as a membrane-like barrier or an encapsulating shell.

In the practice of the present invention, the composition of the invention is placed in or on the environment of use, such as a plant or animal. In many embodiments, the environment of use is the body of an animal. Included in the term "animal" are humans, primates, mammals, domesticated or semi-domesticated animals (such as household, pet, and farm animals), laboratory animals (such as mice, rats and guinea pigs), birds, reptiles, fish, zoo animals, and the like. Typical environments of use within the body include soft tissue such as muscle or fat; hard tissue such as bone; a space, including but not limited to the subcutaneous, peritoneal, periodontal, oral, pulmonary, vaginal, rectal, or nasal space; or a pocket, such as the periodontal pocket or the cul-de-sac of the eye. Alternately, compositions of the present invention may be placed on the body for wound healing, or the transdermal or intradermal delivery of agents and the like.

The compositions of the present invention can be made into various shapes such as flat, square, round, sphere, hemisphere, tubular, cylinder, disc, rod, ring, and the like which can be sized, shaped, and adapted for implantation or insertion in the body, or in cavities and passageways of the body, of an animal. Although in many embodiments the composition will be in the form of implantable rods, discs, or pellets, its applications are not limited to implants and can include smaller injectable microparticles that are thermodynamically unstable but kinetically stable.

The compositions of the present invention may also be in particulate form, which may be delivered directly into the lungs via inhalation. Alternatively, the particulates may be suspended in a suitable suspending vehicle. Examples of suitable suspending vehicles are perfluorinated hydrocarbons, phospholipids, fatty acid esters, mono-, di-, or tri-glycerides, glycerol, polyglycerols, or polyethylene glycols. The resultant suspension may be given by the oral, nasal, parenteral or inhalation routes, or may be applied topically.

Alternately, the compositions of the present invention may be in the form of tablets, suppositories, pastes, creams, films and the like.

The compositions of the present invention can be in the form of a single matrix, a number of matrix layers, or a matrix "membrane" enclosing a reservoir therein.

The compositions of the current invention can be prepared by standard techniques. For example, the sublimable matrix material, the therapeutic agent, and optionally a sublimation rate modifier can be mixed and subsequently extruded into rods, pressed into shaped articles, melt-cast into shaped articles, solvent film cast, melt film cast, compression molded, or formed into microparticles by coacervation or cryogrinding or solvent evaporation for example, and like methods of manufacture.

One method of preparing compositions involves dispersing or dissolving a therapeutic agent and, optionally a sublimation rate modifier, into a molten sublimable matrix material (or mixture of sublimable matrix materials) to form a molten mixture. The molten mixture is then poured into a suitable mold and cooled for use as injectable implants, suppositories, films or tablets, or extruded into rods or sheets for implantable or transdermal devices.

Microparticulate compositions of the current invention may be prepared in a variety of ways. One such method would comprise dispersing or dissolving the therapeutic agent in a molten sublimable matrix material to form a molten mixture, then rapidly combining the molten mixture with a non-solvent for the sublimable matrix material which is combined at a temperature below the melting point of the molten mixture while applying sufficient shear to the molten mixture/non-solvent blend to form microparticles. Alternately the molten mixture could be allowed to cool in a solid mass, which is then reduced to particulate form via ball milling, jet milling, or other methods known-in-the-art. Yet another method to form microparticles would entail dissolving or dispersing a drug in an organic solvent containing a dissolved sublimable matrix material, forming small droplets of this organic phase (containing sublimable matrix material and drug) in a non-miscible phase via high energy mixing, extracting the organic solvent from the droplets and non-miscible phase by a variety of methods known in the art such as evaporation or dilution, and collecting the microparticles.

One particular method of preparing compositions involves mixing a sublimable matrix material, a therapeutic agent and optionally a sublimation rate modifier in a oscillatory ball mill and subsequently compressing the mixture into a suitable shape (pellets, discs, rods, etc.) for use as injectable implants, suppositories for vaginal or rectal use, or tablets for oral use.

It is to be understood in all of the above embodiments that the sublimable solids may be used singly or as mixtures of sublimable solids, and that sublimation rate modifiers may optionally be included. If a sublimation rate modifier is included, it may be homogenously dispersed throughout the matrix, heterogeneously dispersed in order to form pores or a combination thereof, which may facilitate release of the therapeutic agent.

EXAMPLES

The following examples further illustrate the present invention, but should not be construed as in any way limiting its scope. The examples below were carried out using conventional techniques that are well known and routine to those of skill in the art, except where otherwise described in detail.

1. Preparation of Subliming Solids Mixtures

The sublimable matrix materials 2,2,3,3-Tetramethylbutane (hexamethylethane), norbornane, hexamethylcyclotrisiloxane, and adamantane (99%) were purchased from Sigma-Aldrich (St Louis, Mo., USA). Perfluoroneopentane, and perfluoroadamantane were purchased from ExFluor Research (Round Rock, Tex., USA). Hexamethylethane was purified to remove residual pivalic acid by reduced pressure sublimation from a finely powdered mixture of the subliming solid and potassium carbonate. To obtain an intimate mixing of matrix components, an oscillatory ball mill (Retsch MM301 mixer mill and 10 mL stainless steel grinding jars containing 12 mm stainless steel ball bearings) was employed for all milled preparations. Blends of subliming solids were prepared at room temperature by adding a total of either two or three grams of solids to a jar, and milling at 30 Hz for 10 minutes. Either fine powders or glassy masses were obtained upon completion of milling. Glassy masses were hand chopped into small pieces prior to further processing.

2. Preparation of Subliming Solids Matrices

Pellets were prepared by compression molding using a Carver Model C hydraulic press utilizing a 5 mm diameter cylindrical concave faced dye for pellets, a 9 mm concave face die for discs, and a 2 mm diameter dye for rods. Typically, 100-250 mg samples of milled or formulated subliming solid pieces were converted into pellets by room temperature compression at 1000 lbs for 60 seconds. The resulting pellets and rods were 8-10 mm in length. Discs were approximately 9 mm in diameter and approximately 2-4 mm thick. All matrices were translucent to opaque in appearance.

3. Sublimation Rates of Matrices Under Controlled Temperature and Convection

The rates of pellet mass loss were determined gravimetrically by placing a subliming solids matrix pellet or disc on an open pan under freely convective conditions at controlled room temperature. Pans were placed directly onto an analytical balance allowing essentially continuous measurement of pellet weight changes. Sublimation profiles for 150 mg cylindrical pellets of hexamethylethane (HME), adamantane (ADM), perfluoroneopentane(PFNP), norbornane (NOR), hexamethylcyclotrisiloxane (HMC) and perfluoroadamantane (PFA) are shown in FIG. 1.

4. Sublimation Rates of Matrix Blends

Figure 2:
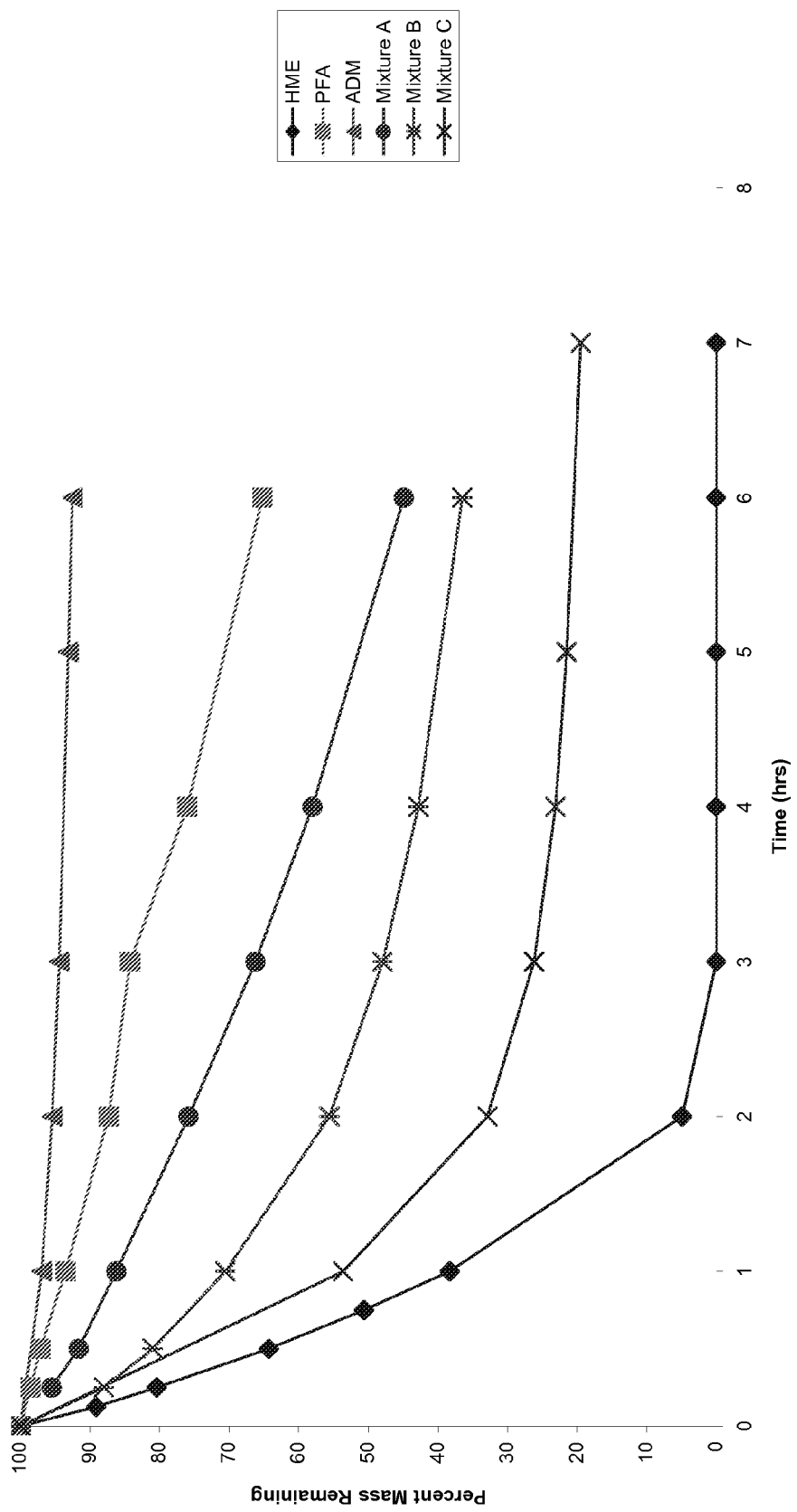

Matrices comprising intimate mixtures or "alloys" of several subliming solids were prepared by ball milling mixture components at 30 Hz for 10 minutes, followed by compression into pellets. Mixture A consisted of 0.6 gm of hexamethylethane, 0.6 gm of adamantane, and 0.6 gm perfluoroadamantane. Mixture B consisted of 0.5 gm hexamethylethane, 0.5 gm adamantane, and 2.1 gm of perfluoroadamantane. Mixture C consisted of 1 gm hexamethylethane, 0.5 gm adamantane and 0.5 gm perfluoroadamantane. Pellets of each mixture were prepared by compression molding 110-115 mg aliquots of Mixture A, 150-165 mg aliquots of Mixture B and 120-150 mg aliquots of Mixture C at 1000 lbs for 60 seconds. Sublimations were performed at room temperature in open pans as in Example 3. The sublimation rates of the matrices are shown in FIG. 2.

5. Sublimation Rate Modifiers on Erosion Rates of Subliming Solids Matrices

Figure 3:
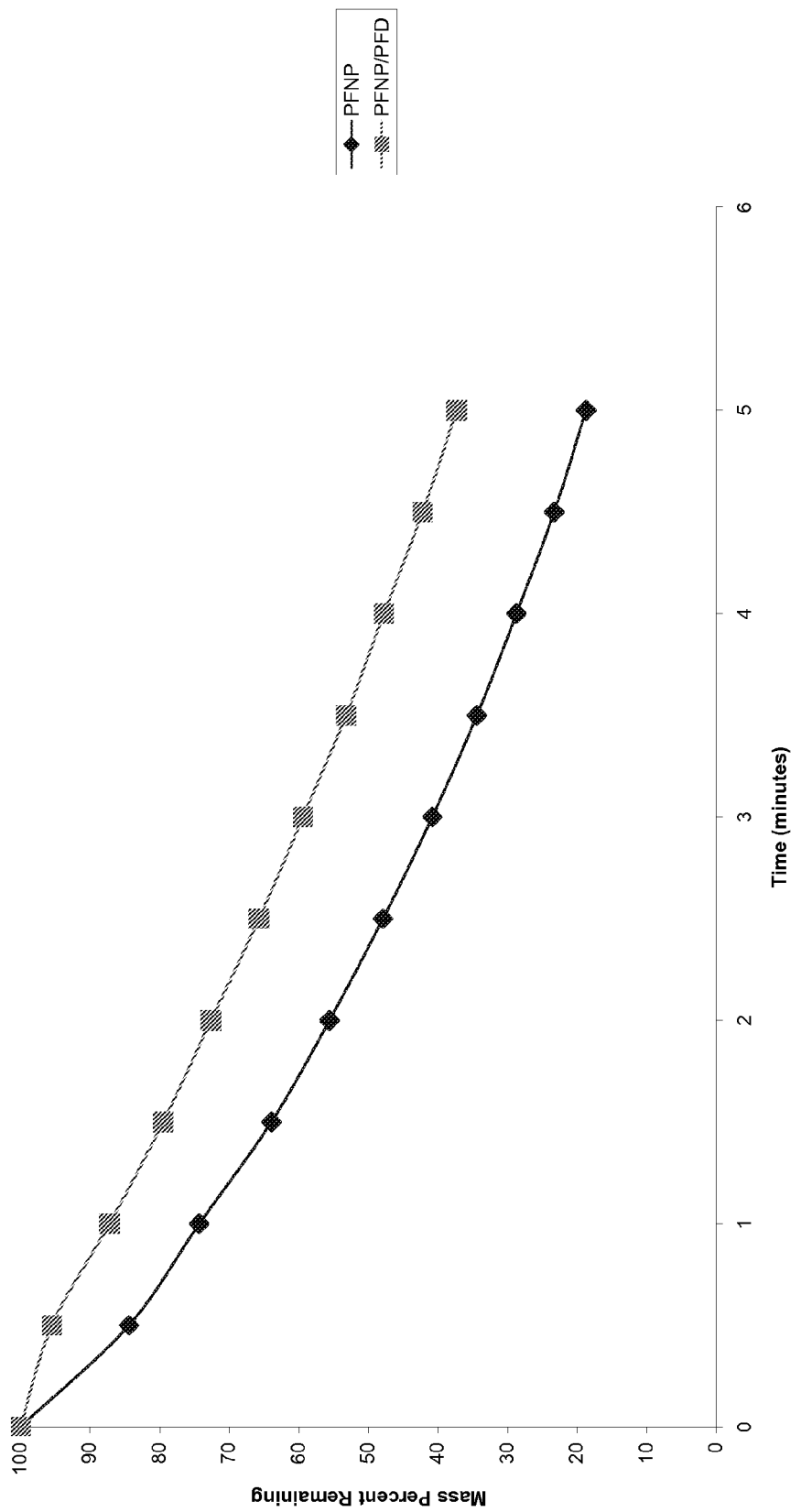

Perfluoroneopentane (PFNP) matrices containing 25% perfluorodecalin (PFD) by weight were prepared by blending 1.5 grams of solid perfluoroneopentane with 500 mg of liquid perfluorodecalin. Oscillatory ball milling at 30 Hz for 10 minutes yielded a soft plastic solid. Cylindrical pellets of 150 mg were prepared by compression at 1000 lbs for 60 seconds. Sublimation was measured as in Example 3, with the reduced rate of matrix erosion being shown in FIG. 3.

6. In Vitro Release Rate of Bromophenol Blue from Cylindrical Pellets of Subliming Hexamethylethane Matrix Bromophenol blue sodium salt (BPB) was purchased from Sigma-Aldrich (St Louis, Mo., USA), and dispersed into hexamethylethane by blade milling approximately 30 mg of accurately weighed dye into approximately 3.0 g of accurately weighed subliming solid, at room temperature. Target loading of bromophenol blue was 1% by weight (0.98-1.22% actual). Cylindrical pellets of the formulated hexamethylethane matrix were prepared by molding 150 mg of cohesive powder into 5 mm×9 mm cylinders by room temperature compression at 1000 lbs for 60 seconds.

Figure 4:
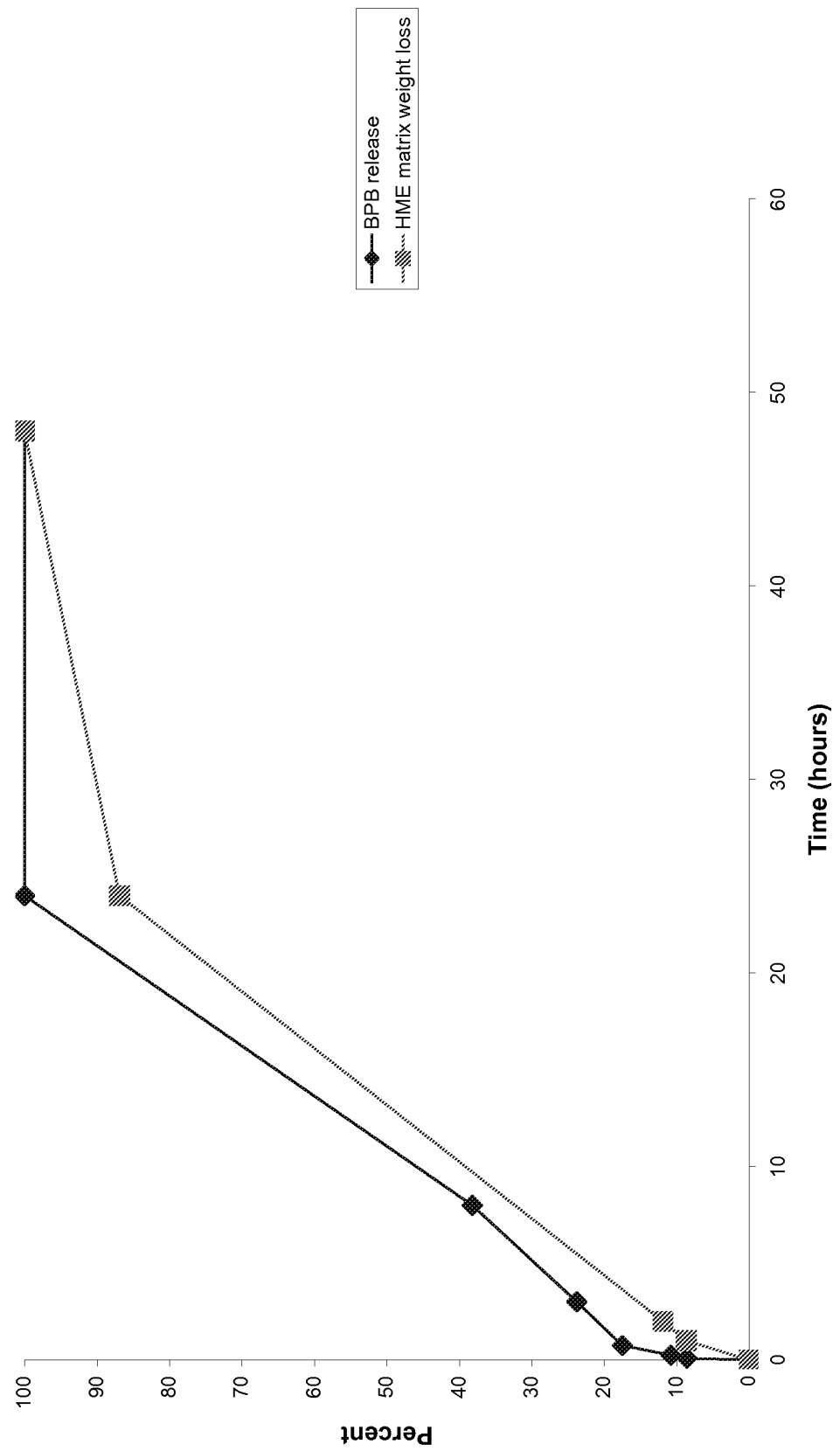

The amount of bromophenol blue (BPB) released from pellets into 10 mL of deionized water under constrained sublimation/convection conditions, namely in open (150×15 mm) test tubes incubated at 37° C. in an oscillating (86 rpm) water bath, was determined by cumulative absorbance measurements at 497 nm (the isosbestic point of BPB) over a series of time intervals, under sink conditions for the solute. Evaporated water volumes were replaced prior to aliquot withdrawals for absorbance measurements. Percents of BPB released at given time points were calculated relative to final absorbance measured upon complete pellet disappearance. The rates of pellet sublimation were determined by recovering, patting dry, and weighing at each time point. Absorbances and weight changes were measured for duplicate or triplicate pellet samples, with mean percents released and weight lost at defined time points being reported. The data, demonstrating the equivalence of BPB release rate to matrix sublimation rate, are shown in FIG. 4.

Figure 5:
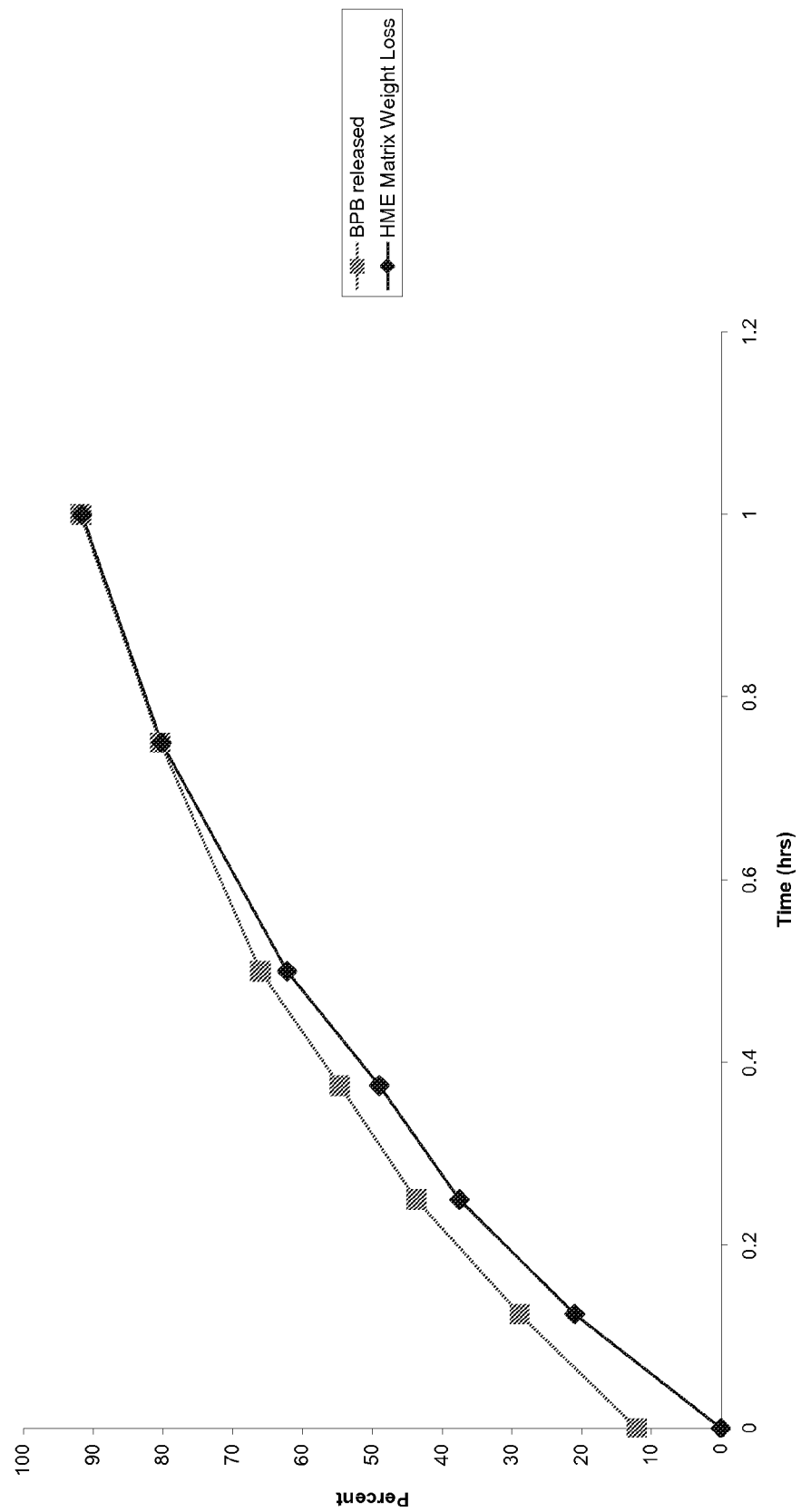
Figure 6:
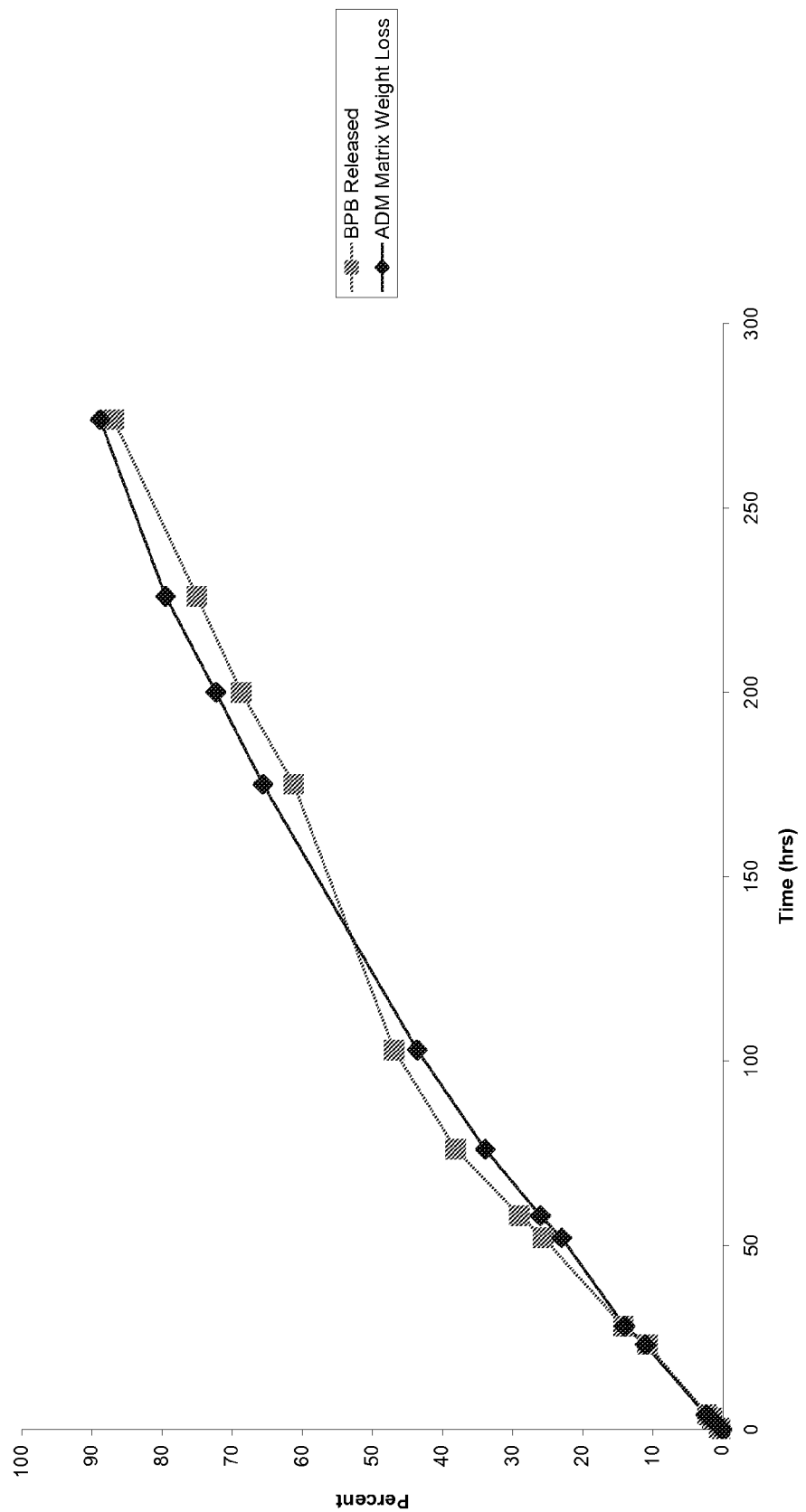

7. In Vitro Release Rates of Bromophenol Blue from Thin Disc Hexamethylethane and Adamantane Matrices Formulations of 5% bromophenol blue in hexamethylethane and adamantane were prepared by oscillatory ball milling 1.9 grams of each subliming solid with 100 mg of dye for 20 minutes at 30 Hz. The resultant mixtures were both more adhesive and cohesive than the materials obtained by milling of the pure subliming solids. Discs of each formulation were prepared by compressing 200 mg of material in a 9 mm diameter cylindrical die with 1000 lbs pressure for 10 minutes at room temperature. The rate of disc sublimation was determined gravimetrically using open pans at room temperature (Example 3), and the rate at which bromophenol blue was released from the matrix as it sublimed was determined after each weighing by immersing each disc in 10 mL of deionized water for 5 seconds, then patting dry and resuming sublimation into air. Absorbances of dye solutions obtained at each time point were measured at 497 nm, diluting where necessary to maintain measured absorbances below 1.5. Equivalent rates of cumulative dye release and matrix weight loss are shown in FIG. 5 for hexamethylethane and FIG. 6 for adamantane. In both cases, disc sublimation rate and dye release rates were essentially identical 8. In Vitro Release Rates of Betamethasone from Subliming Solids Matrices Betamethasone (Sigma Aldrich, St Louis Mo. USA) was incorporated into hexamethylethane (HME), adamantane (ADM), and a 50/50 weight percent HME/ADM matrices by oscillatory ball milling approximately 2 g of accurately weighed subliming solid (or subliming solid mixtures) with approximately 44 mg of accurately weighed steroid in 10 mL grinding jars. Milling was performed at room temperature for 3 minutes at an oscillation speed of 30 Hz. The target loading of betamethasone was 2.2% by weight (2.1-2.7% actual). Pellets of each drug-containing mixture were prepared by compression molding using a Carver Model C hydraulic press and 5 mm diameter cylindrical concave faced dyes. Typically, 80 mg aliquots of each mixture were converted into pellets by room temperature compression at 1000 lbs for 60 seconds. Resulting pellets were 5 mm in diameter, 7-9 mm in length and translucent to opaque in appearance.

Betamethasone release from the pellets was measured: (1) under constrained sublimation/convection conditions, wherein pellets were immersed in 10 mL of deionized water in open 150×15 mm test tubes; (2) under conditions where sublimation into air could not occur, wherein pellets were immersed in 15 mL of deionized water in completely filled and sealed 125×10 mm test tubes; or (3) where pellets were incubated in open, empty 150×15 mm test tubes. Duplicate or triplicate samples for each storage condition were incubated at 37° C. in an oscillating (86 rpm) water bath. At defined time points 1 mL aliquots of the release solution were removed for quantitation of betamethasone, with the entire volume of release medium (water) being replaced at every measurement time point. Sink conditions (<25% of saturation) were maintained for all drug release intervals. At the same defined time points, the rate of pellet sublimation from empty test tubes were determined gravimetrically.

Amounts of betamethasone released into aqueous release medium were measured by assaying sets of solution samples using reverse phase HPLC. Briefly, 10 uL injections of release medium were made onto an YMC-Pack ODS-A column (5 micron, 6.0×150 mm) and eluted at 1.2 mL/minute with a 50 mM potassium dihydrogen phosphate/methanol (45/55 v/v) mobile phase, at a temperature of 40° C., for 20 minutes. Betamethasone was detected at 240 nm.

Figure 7:
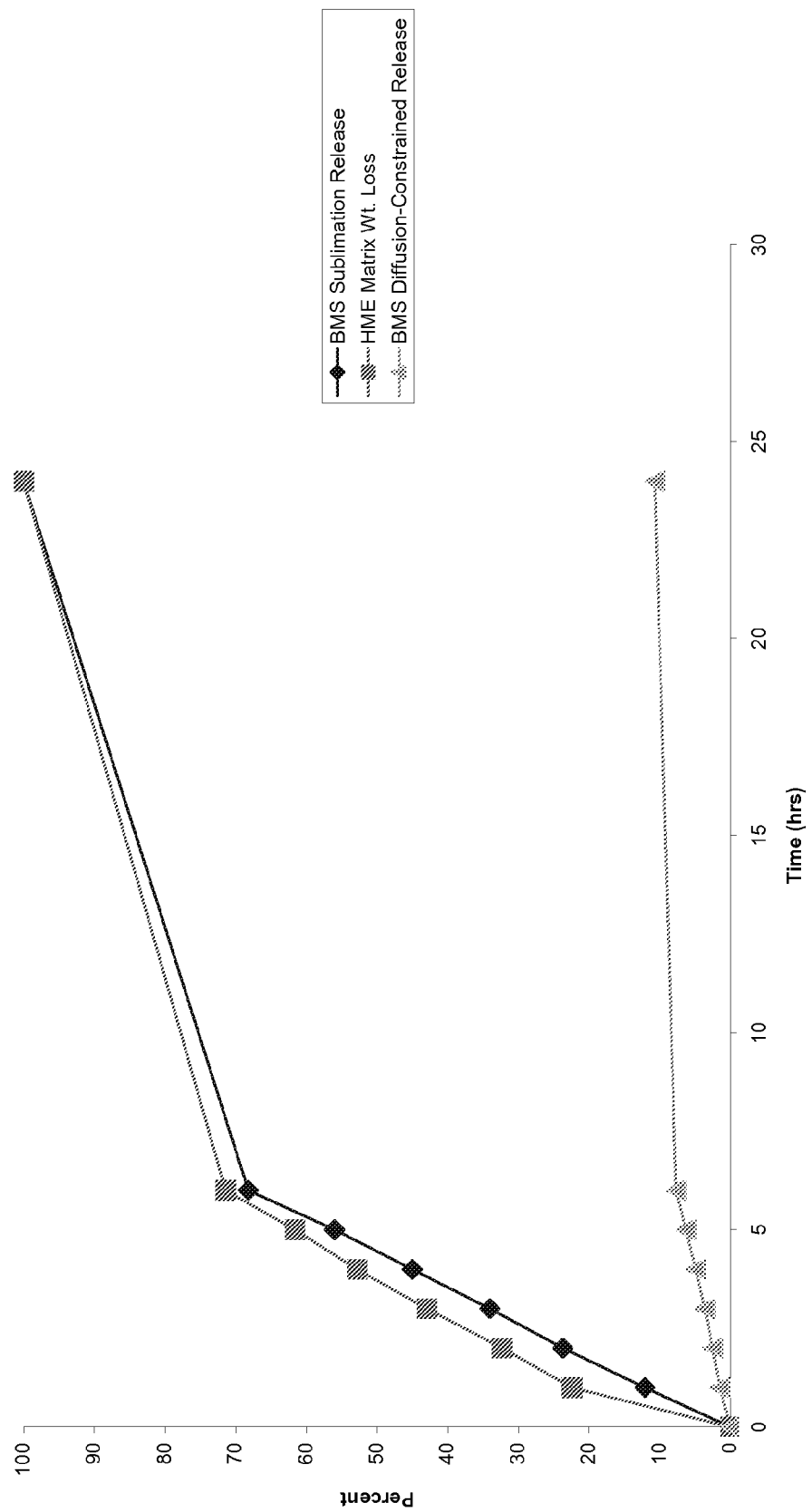
Figure 8:
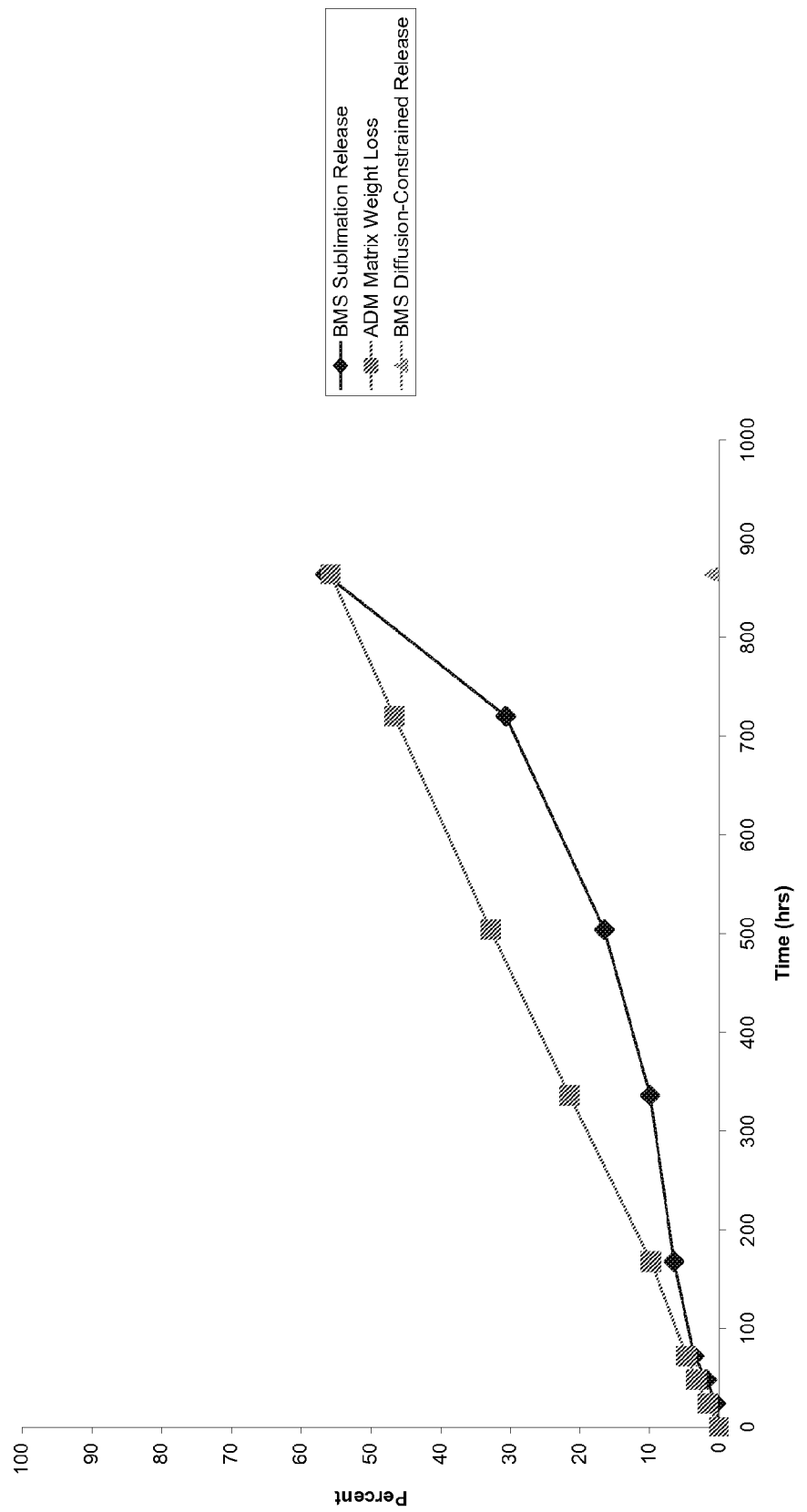
Figure 9:
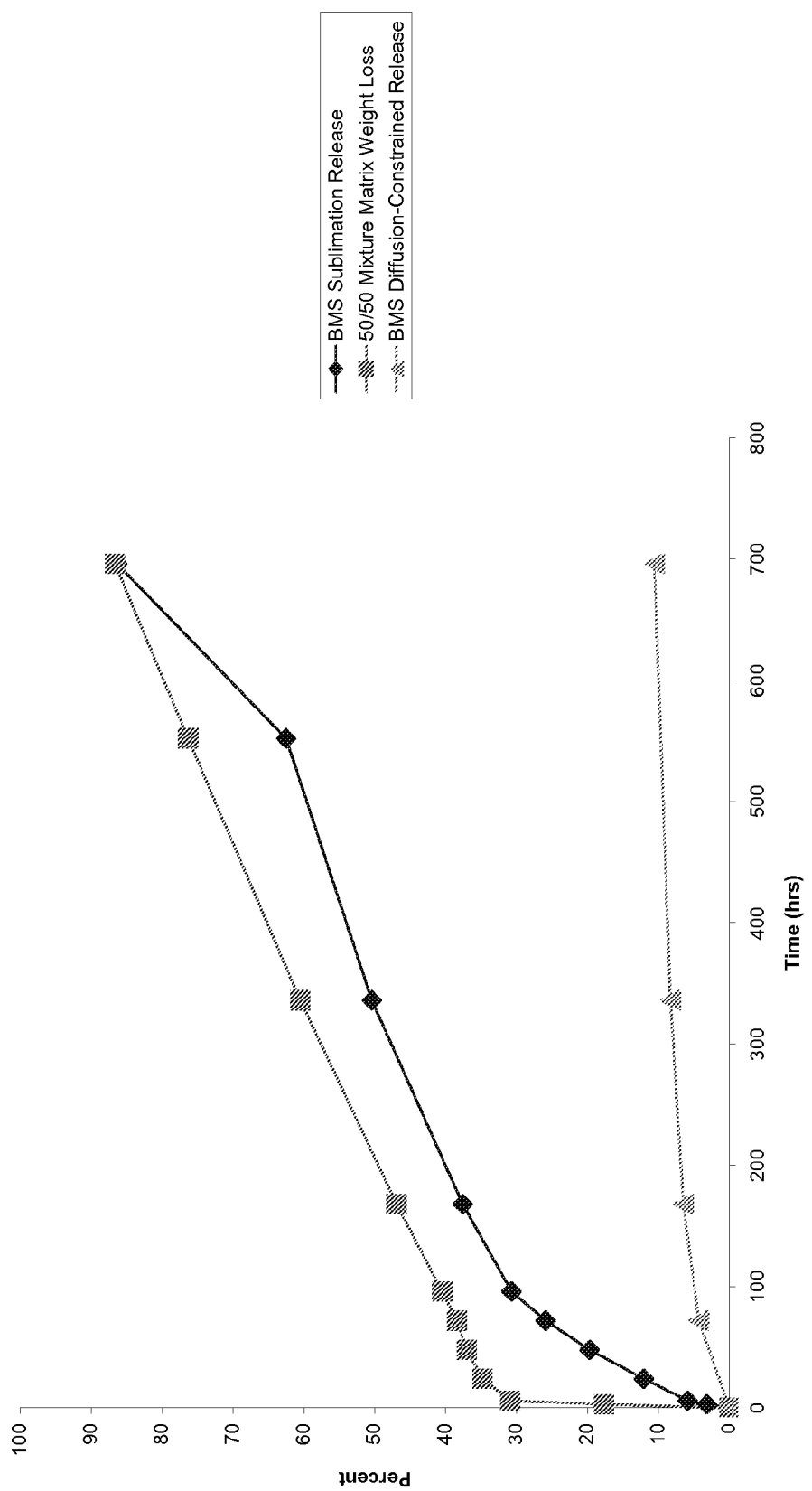

The mean percent of drug released and the mean pellet weight lost at defined time points for hexamethylethane, adamantane, and 50/50 HME/ADM mixture pellets are shown in FIGS. 7, 8, and 9 respectively, and demonstrate that the release rates of betamethasone from pellets into deionized water were very similar to the sublimation rates into air of all three pellet matrices. The rates of betamethasone released from pellets stored under conditions where sublimation did not occur, i.e., in water-filled sealed tubes, where drug release can only occur via dissolution of the drug followed by its diffusion through the pellet matrix, was in every case much slower than from subliming pellets.

Figure 10:
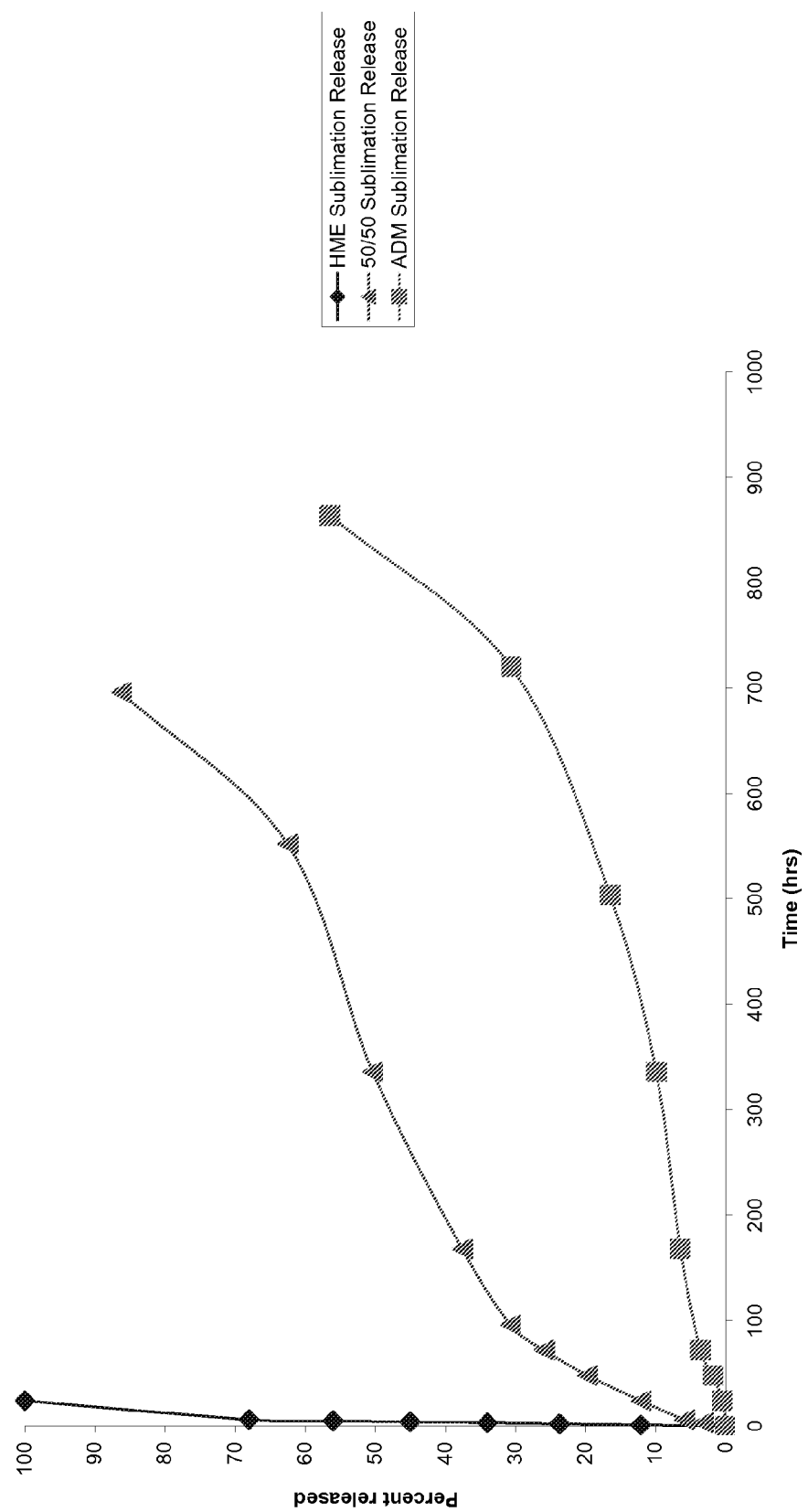

The effect of blending subliming solid matrices to modulate release is shown in FIG. 10, which demonstrates that the mixing of two subliming matrices can yield release profiles intermediate to those of the pure subliming solids.

9. In Vivo Sublimation Rates of Subliming Solids Matrices

Figure 11:
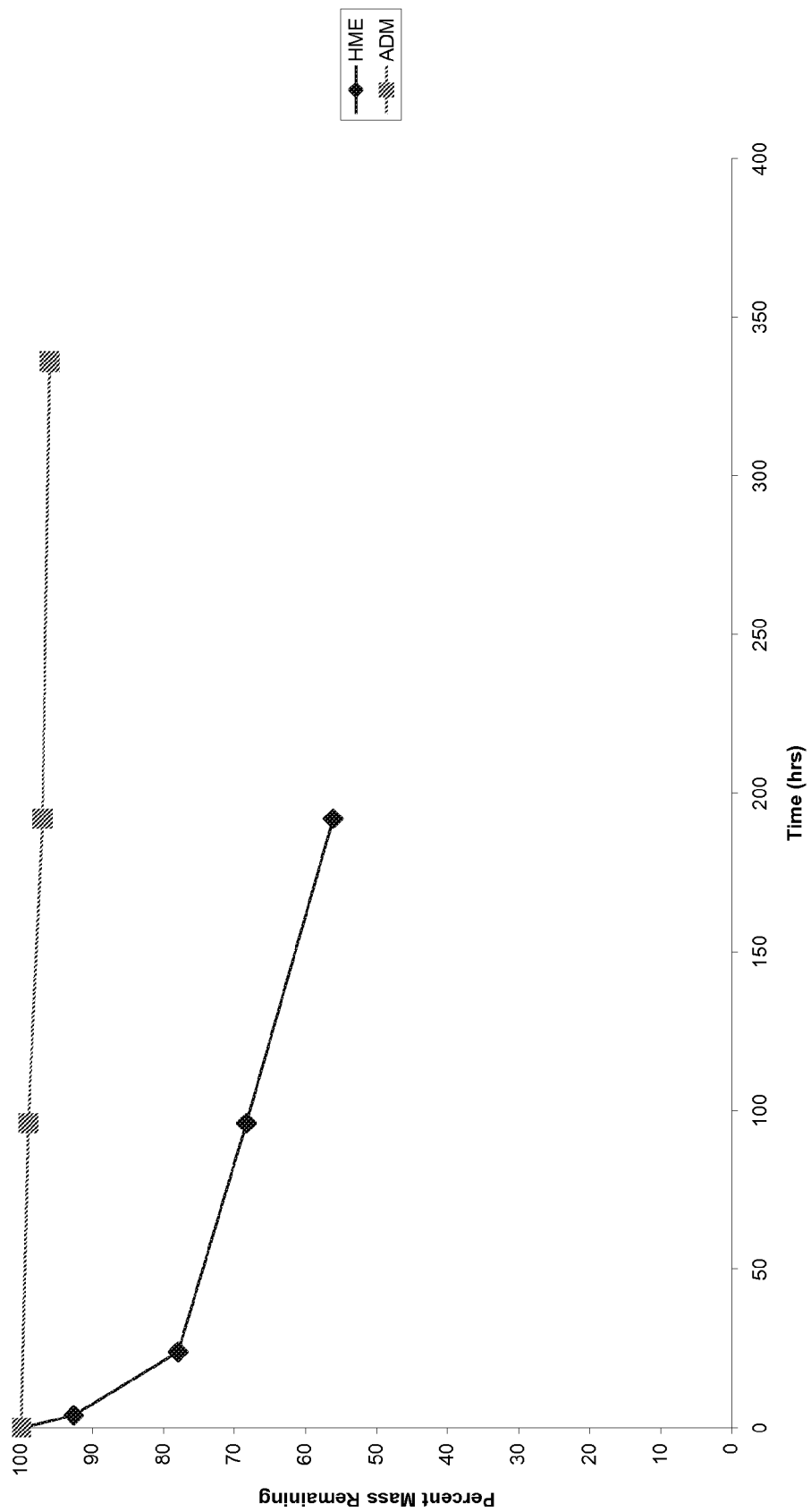
FIG. 11 illustrates the in-vivo sublimation rate of HME and ADM pellets, as measured by the percent of the explanted pellet mass remaining versus time.

The in-vivo disappearance rates of hexamethylethane and adamantane pellets from subcutaneous implant sites in rats were assessed over a 16-week period. Forty six Sprague-Dawley male rats of similar age and weight were assigned into five treatment groups: hexamethylethane pellet implantation (Group H), adamantane pellet implantation (Group A), PLGA (Boehringer Ingelheim Resomer RG 504H) pellet implantation (Group P), a sham group for which surgery was performed without pellet implantation, and a control (no surgery) group. Pellets were individually weighed, and implanted into the neck scruff of rats. Explantation and reweighing of adamantane pellets was performed at 4 and 8 days, and 2, 4, 8, and 10 weeks; hexamethylethane pellets were explanted and weighed at 4 and 24 hours, and 4, 8, and 14 days. FIG. 11 demonstrates that in the in-vivo sublimation of hexamethylethane matrix pellets can occur over a period as short as one week, with disappearance of adamantane pellets occurring over a period of at least two months.

10. In Vivo Release Rates of Bioactive Interferon Alpha from Subliming Solids Matrices Recombinant human interferon alfa-2b ($\alpha$-IFN) was incorporated into matrices comprised of either hexamethylethane, adamantane, or a 50/50 mixture of hexamethylene and adamantane by oscillatory ball milling. A uniform, fine dispersion of lyophilized $\alpha$-IFN particles in each matrix was prepared by combining approximately 23 mg of lyophilized $\alpha$-IFN powder (containing 50 MIU of $\alpha$-IFN) with 2.1-2.2 grams of the subliming solid, and milling at 30 Hz for 45 seconds. The subliming solids mixture matrix was prepared by milling 1.59 grams of hexamethylethane with 1.50 grams of adamantane, at 30 Hz for ten minutes.

Uniformity of the dispersion of the protein throughout the matrix was demonstrated by microscopic evaluation of a model protein, rhodamine-labelled bovine serum albumin, which was dispersed in hexamethylene or adamantane matrices by the techniques described above. No discrete particles of rhodamine-labelled protein were detected at 200× magnification, upon incident illumination with blue light. The absence of visible protein particulates was also observed in adamantane matrices.

Each milligram of post-milled matrix typically contained 22,700 IU of interferon and 0.011 mg of water-soluble species (glycine, phosphates, and human serum albumin), corresponding to weight percent loadings of 0.01% interferon and 1.1% water soluble solids. Cylindrical pellets of the three interferon containing matrices were prepared by compressing 150 mg samples of accurately weighed subliming solids mixture with 1000 lbs of pressure for 60 seconds.

Subcutaneous implantation of pellets (typically containing 3.2 MIU of interferon alpha) into rats was performed as described in Example 9. Ten animals were assigned to each subliming solids matrix group, with each pellet being assigned to a specific rat having a known initial (and final) weight. Subsequent to implantation, 1 mL blood samples were drawn at specific time points, reduced to serum, and stored frozen at −70 degrees prior to analysis. Sampling time points for rats dosed with hexamethylethane pellets were 1, 2, 6, and 24 hours, 2, 3, 4, 7, 10, 14, and 21 days. Rats implanted with adamantane and 50% mixture pellets had additional blood samples drawn at 4, 5, 6, 8, and 10 weeks.

Soluble human interferon-alpha concentrations in serum samples from each of ten rats were determined using a calorimetric ELISA with anti-secondary antibody conjugated to horseradish peroxidase and tetramethyl benzidine as substrate. Assays were performed by PBL Biomedical Laboratories (Piscataway N.J.). Interferon biological activity present in each sample was determined using a MDBK cell based VSV virus inhibition assay, with analyses again being performed by PBL Biomedical Laboratories.

Figure 12:
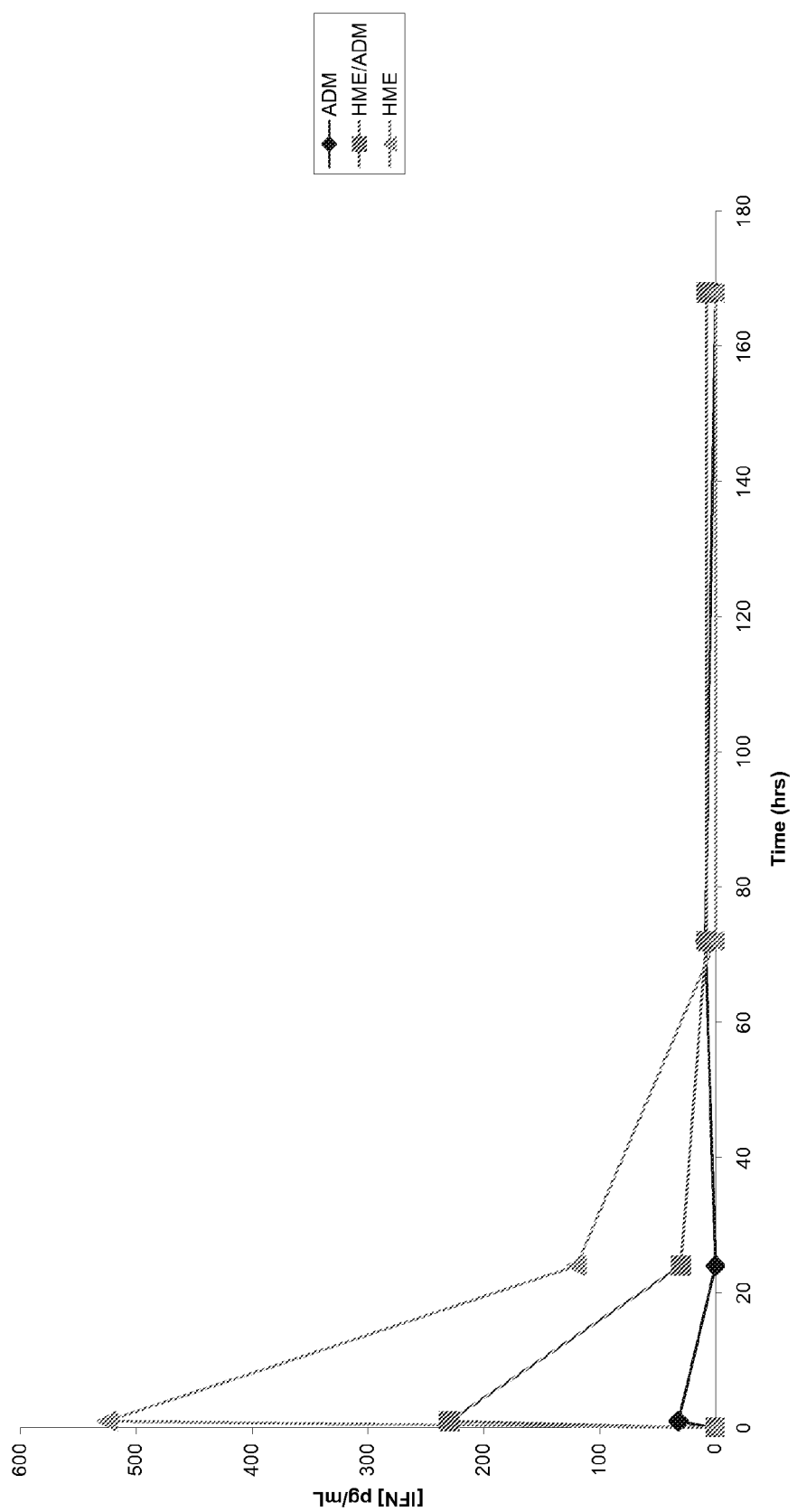
FIG. 12 is a graph of the serum concentration (pg/mL) of recombinant human interferon alfa-2b ($\alpha$-IFN) in rats, after subcutaneous administration of $\alpha$-IFN containing pellets comprised respectively of HME, ADM, and HME/ADM mixture matrices.

Results of the above study, demonstrating sustained in vivo release of soluble and biologically active interferon alpha from hexamethylethane, adamantane, and 50/50 mixture matrices, are shown in FIG. 12. Calculation of first order rate constants from these data demonstrate slower release from the ADM matrix, $k=0.017$ $hr^{-1}$, than from the HME matrix, $k=0.064$ $hr^{-1}$.

The previous description of the preferred embodiments is provided to enable any person skilled in the art to make and use the present invention. The various modifications to these embodiments will be readily apparent to those skilled in the art, and the generic principles defined herein may be applied to other embodiments without the use of the inventive faculty. Thus, the present invention is not intended to be limited to the embodiments shown herein but is to be accorded the widest scope consistent with the principles and novel features disclosed herein.

11. Enhancement of Alkaline Phosphatase Stability Under Physiological Conditions by Incorporation of the Protein into Hexamethylethane Matrices Alkaline phosphatase (ALP) was obtained as a lyophilized powder formulation containing 24 U/mg of enzyme activity (Sigma-Aldrich Corp., Cat. No. P-5931). ALP was incorporated into HME matrices by first blending 10.5 mg of the enzyme powder with 3.0 grams of HME in an oscillatory ball mill at 30 Hz for 45 seconds, and forming rod-type matrices by compressing 60-70 mg samples of the blend at 1000 pounds for 60 seconds. The matrices were then stored in water-filled and sealed 2 mL polyethylene vials, and incubated at 37° C. Concomitantly, ALP lyophilized powder samples were incubated at 37° C. and 100% relative humidity in open polyethylene vials. Samples stored under each condition were pulled at defined time intervals, with rods being removed from water filled vials, dried, and then stored at room temperature in new open vials for 24 hours, in order to sublime away all matrix material. The vials were then sealed and stored at −20° C. until assayed for activity (see below). Vials containing the lyophilized enzyme powder were directly sealed upon removal from the water bath and stored at −20° C. degrees until assayed.

Specific and total activity in vials was measured using a kinetic p-nitrophenyl phosphate hydrolysis assay (QuantiChrom Alkaline Phosphatase Assay Kit, BioAssay Systems, Hayward Calif.). Analysis of each phosphatase sample was performed in triplicate. The results, shown in FIG. 13 as percents of initial activity remaining over time, demonstrate that the rate of enzyme activity loss under physiological conditions can be significantly reduced when the enzyme powder is dispersed in a subliming solids matrix.

What is claimed is:

1. A matrix biological insert or implant which is a delivery system suitable for sustained release of a biologically active agent within a mammal, said delivery system comprising:
    (a) at least one water insoluble sublimable matrix material that converts to vapor at a desired rate over a desired duration in the body of a mammal; and
    (b) a biologically active agent dispersed within said sublimable matrix material in an amount of 0.05 to 40% by weight based on a weight of said delivery system sufficient for prolonged treatment of a disease or other pathological condition in said mammal,
    wherein said sublimable matrix material has a sublimation enthalpy in a range of from 20 to 100 kJ/mole and is present in an amount of at least 60% by weight based on a weight of said delivery system effective to achieve a sustained release of said active agent in said mammal upon conversion of said sublimable matrix material to said vapor, and
    wherein said sublimable matrix material is selected from the group consisting of adamantane, perfluoroadamantane, 1-methyladamantane, perfluoro-1-methyladamantane, tetraisopropylmethane, perfluorotetraisopropylmethane, 2,2,3,3-tetramethylbutane (hexamethylethane), perfluoro-2,2,3,3-tetramethylbutane, perfluoroneopentane, perfluoro-C60fullerene, cubane, perfluorocubane, octamethylcubane, perfluorooctamethylcubane, perfluoromethyladamantane, perfluorotri-tert-butylmethane, perfluorodimethyladamantane, perfluorohexamethylethane, perfluoro-1,3-dimethyladamantane, isocamphane, tricyclene, 1-ethyladamantane, 1-methyldiadamantane, perfluorodimethylbicyclo[3.3.1]nonane, diadamantane, perfluorodiadamantane, tri-tert-butylmethane, norbornane, perfluoronorbornane, cyclododecane, perfluorocyclododecane, hexamethylcyclotrisiloxane, perfluoroundecane, perfluorododecane, bicyclo[3.3.1]nonane, tetracycloheptane, tricyclohexane, dimethyl-isopropylperhydrophenanthrene, hexamethylprismane, prismane, tetracyclododecane, bicyclo[3.3.3]undecane, 2-methyladamantane, pentacycloundecane, tricyclodecane, bicyclodecane, bicyclo[2.2.2]octane, perfluoro-1,3,5-trimethyladamantane, perfluoro-2,2-dimethyladamantane, perfluorotetracycloheptane, perfluorotricyclohexane, perfluorohexamethylprismane, perfluoroprismane, perfluorotetracyclododecane, perfluorobicyclo[3.3.3]undecane, perfluoro-2-methyladamantane, perfluoropentacycloundecane, perfluorotricyclodecane, perfluorobicyclodecane, perfluorobicyclo[3.3.1]nonane, perfluorobicyclo[2.2.2]octane, perfluorobicyclo[2.2.1]heptane, and mixtures thereof.

2. A matrix biological insert or implant which is a delivery system suitable for sustained release of a biologically active agent within a mammal, said delivery system comprising:
    (a) at least one water insoluble sublimable matrix material that converts to vapor at a desired rate over a desired duration in the body of a mammal; and
    (b) a biologically active agent dispersed within said sublimable matrix material in an amount of 0.05 to 40% by weight based on a weight of said delivery system sufficient for prolonged treatment of a disease or other pathological condition in said mammal,
    wherein said sublimable matrix material has a sublimation enthalpy in a range of from 20 to 100 kJ/mole and is present in an amount of at least 60% by weight based on a weight of said delivery system effective to achieve a sustained release of said active agent in said mammal upon conversion of said sublimable matrix material to said vapor, and wherein said sublimable matrix material is selected from the group consisting of hexamethylcyclotrisiloxane, cyclododecane, perfluorododecane, perfluorododecane or mixtures thereof.

3. A matrix biological insert or implant that delivers a biologically active agent within a mammal, said insert or implant comprising:
(a) at least one water insoluble sublimable matrix material that converts to vapor at a desired rate over a desired duration in the body of a mammal, wherein said sublimable matrix material is selected from the group consisting of adamantane, perfluoroadamantane, 1-methyladamantane, perfluoro-1-methyladamantane, tetraisopropylmethane, perfluorotetraisopropylmethane, 2,2,3,3-tetramethylbutane (hexamethylethane), perfluoro-2,2,3,3-tetramethylbutane, perfluoroneopentane, perfluoro-C60 fullerene, cubane, perfluorocubane, octamethylcubane, perfluorooctamethylcubane, perfluoromethyladamantane, perfluorotri-tert-butylmethane, perfluorodimethyladamantane, perfluorohexamethylethane, perfluoro-1,3-dimethyladamantane, isocamphane, tricyclene, 1-ethyladamantane, 1-methyldiadamantane, perfluorodimethylbicyclo[3.3.1]nonane, diadamantane, perfluorodiadamantane, tri-tert-butylmethane, norbornane, perfluoronorbornane, cyclododecane, perfluorocyclododecane, hexamethylcyclotrisiloxane, perfluoroundecane, perfluorododecane, bicyclo[3.3.1]nonane, tetracycloheptane, tricyclohexane, dimethyl-isopropylperhydrophenanthrene, hexamethylprismane, prismane, tetracyclododecane, bicyclo[3.3.3]undecane, 2-methyladamantane, pentacycloundecane, tricyclodecane, bicyclodecane, bicyclo[2.2.2]octane, perfluoro-1,3,5-trimethyladamantane, perfluoro-2,2-dimethyladamantane, perfluorotetracycloheptane, perfluorotricyclohexane, perfluorohexamethylprismane, perfluoroprismane, perfluorotetracyclododecane, perfluorobicyclo[3.3.3]undecane, perfluoro-2-methyladamantane, perfluoropentacycloundecane, perfluorotricyclodecane, perfluorobicyclodecane, perfluorobicyclo [3.3.1]nonane, perfluorobicyclo[2.2.2]octane, perfluorobicyclo[2.2.1]heptane, and mixtures thereof; and
(b) a biologically active agent dispersed in said sublimable matrix material in an amount of 0.05 to 40% by weight based on a weight of said delivery system sufficient for prolonged treatment of a disease or other pathological condition in a mammal, wherein said sublimable matrix material has a sublimation enthalpy in a range of from 20 to 100 kJ/mole and is present in an amount of at least 60% by weight based on a weight of said insert or implant effective to achieve a sustained release of said active agent in said mammal upon conversion of said sublimable matrix material to said vapor, wherein said insert or implant is compressed into a predetermined size and shape, is chemically inert, and is biocompatible.

4. The biological insert or implant of claim 3 wherein said sustained release of said active agent within said mammal occurs for a period of about 7 days.

5. The biological insert or implant of claim 3 further comprising a sublimation rate modifier selected from the group consisting of trimethylacetamide, 2,2-dimethyl-1,3-propanediol, neopentylpivalate, perfluorodecalin, tri-tert-butylmethanol, camphor, camphene, neo-pentyl alcohol, hexachloroethane, chlorobutanol, menthol, terpin hydrate, vanillin, ethyl vanillin, 1,3,5-trioxane, naphthalene, phenol, dextran, glycogen, tert-butanol, biodegradable polymers comprised of polylactic acid or copolymers of lactic and glycolic acids, polyorthoesters, or polyanhydrides, microparticles comprised of said biodegradable polymers, fatty acids, polyvinylpyrrolidone, polyethyleneglycol, polyvinyl alcohol, polyacrylic acid, cholesterol and microparticles thereof, triglycerides having a melting point above 37° C., collagen and microparticles thereof, gelatin and microparticles thereof, ethanol, propylene glycol, PEG 400, glycerol, polyglycerol, polysorbates, sucralose, sucralose pentahydrate, and mixtures thereof.

6. The biological insert or implant of claim 3 wherein said predetermined shape of said insert or implant is a disk, a cylinder, a rod, a ring or a pellet.

7. The biological insert or implant of claim 3 wherein said amount of said sublimable matrix material is at least 80% by weight based on the weight of said insert or implant.

8. The biological insert or implant of claim 3 wherein said sustained release of said active agent within said mammal occurs for a period of about 30 days.

9. The biological insert or implant of claim 3 wherein said sustained release of said active agent within said mammal occurs for a period of about 3 months.

10. The biological insert or implant of claim 3 which is a biological implant.

* * * * *

UNITED STATES PATENT AND TRADEMARK OFFICE
CERTIFICATE OF CORRECTION

PATENT NO. : 9,301,919 B2  
APPLICATION NO. : 11/615048  
DATED : April 5, 2016  
INVENTOR(S) : Maskiewicz Page 1 of 1

It is certified that error appears in the above-identified patent and that said Letters Patent is hereby corrected as shown below:

Column 14, line 66 of the specification, the text "150" should read -- ~150 --

Signed and Sealed this  
Twenty-eighth Day of June, 2016

Michelle K. Lee  
*Director of the United States Patent and Trademark Office*